(12) United States Patent
Chambers et al.

(10) Patent No.: US 7,094,777 B2
(45) Date of Patent: Aug. 22, 2006

(54) 5-HT$_{2A}$ RECEPTOR LIGANDS

(75) Inventors: Mark Stuart Chambers, Puckeridge (GB); Neil Roy Curtis, Buntingford (GB); Angus Murray MacLeod, Bishops Stortford (GB); Robert James Maxey, Amersham (GB); Helen Jane Szekeres, Bisley (GB)

(73) Assignee: Merk Sharp & Dohme Ltd., Hoddesdon ( * ) Notice: Subject to any disclaimer, the term of this patent is extended or adjusted under 35 U.S.C. 154(b) by 0 days.

(21) Appl. No.: 10/984,249

(22) Filed: Nov. 9, 2004

(65) Prior Publication Data
US 2005/0101586 A1 May 12, 2005

(30) Foreign Application Priority Data
Nov. 10, 2003 (GB) ................ 0326221.9

(51) Int. Cl.
*A61K 31/397* (2006.01)
*C07D 275/04* (2006.01)
*C07D 261/20* (2006.01)
*C07D 205/04* (2006.01)

(52) U.S. Cl. ............... 514/210.01; 514/210.21; 548/207; 548/217; 548/950

(58) Field of Classification Search .......... 548/950, 548/952, 207, 217; 514/210.01, 210.21
See application file for complete search history.

(56) References Cited

U.S. PATENT DOCUMENTS

| 4,128,552 | A | 12/1978 | Wise et al. |
| 4,218,455 | A | 8/1980 | Wise et al. |
| 6,194,406 | B1 * | 2/2001 | Kane et al. ............. 514/218 |
| 6,479,279 | B1 | 11/2002 | Achard et al. |
| 6,479,479 | B1 | 11/2002 | Achard et al. |
| 6,872,717 | B1 | 3/2005 | Achard et al. |

FOREIGN PATENT DOCUMENTS

| EP | 0261688 | 9/1987 |
| EP | 0304888 | 8/1988 |
| EP | 0330826 | 1/1989 |
| WO | WO 96/35666 | 4/1996 |
| WO | WO 00/43362 | 7/2000 |

OTHER PUBLICATIONS

S. Fletcher, et al, "4-(Phenylsulfonyl)piperidines: Novel, Selective, and Bioavailable 5-HT2A Receptor Antagonists", J. Med. Chem., 25, 492-503 (2002).

* cited by examiner

*Primary Examiner*—Kamal Saeed
*Assistant Examiner*—Michael P. Barker
(74) *Attorney, Agent, or Firm*—J. Eric Thies; Melvin Winokur

(57) ABSTRACT

Compounds of formula I:

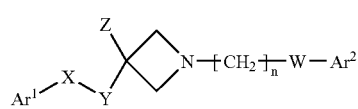

are antagonists of the human 5-HT$_{2A}$ receptor, and hence useful in treatment or prevention of a variety of neurological conditions.

24 Claims, No Drawings

5-HT$_{2A}$ RECEPTOR LIGANDS

CROSS REFERENCE TO RELATED APPLICATIONS

This application claims priority under 35 U.S.C. § 119 from GB Application No. 0326221.9, filed Nov. 10, 2003.

The present invention relates to a class of azetidine derivatives which act on serotonin receptors (also known as 5-hydroxytryptamine or 5-HT receptors). More particularly, the invention concerns 1-(arylalkyl)-substituted azetidine derivatives comprising additional substitution at the 3-position. These compounds are potent and selective antagonists of the human 5-HT$_{2A}$ receptor and are therefore useful as pharmaceutical agents, especially in the treatment and/or prevention of adverse conditions of the central nervous system, including sleep disorders such as insomnia and psychotic disorders such as schizophrenia and psychiatric disorders such as anxiety.

Compounds of the invention may display more effective binding to the human 5-HT$_{2A}$ receptor than to other human receptors such as D$_2$, 5HT$_{2C}$ and IKr receptors. They can therefore be expected to manifest fewer side-effects than compounds which do not discriminate in their binding affinity between such receptors. In addition these compounds have lower effects on the IKr receptors and there is a separation of the desired effect from side effects such as cardiac effects.

By virtue of their potent human 5-HT$_{2A}$ receptor antagonist activity, the compounds of the present invention are effective in the treatment of neurological conditions including sleep disorders such as insomnia, psychotic disorders such as schizophrenia, and also depression, anxiety, panic disorder, obsessive-compulsive disorder, pain, eating disorders such as anorexia nervosa, and dependency or acute toxicity associated with narcotic agents such as LSD or MDMA; and moreover are beneficial in controlling the extrapyramidal symptoms associated with the administration of neuroleptic agents. They may further be effective in the lowering of intraocular pressure, and may also be effective in treating menopausal symptoms, in particular hot flushes (see Waldinger et al, *Maturitas*, 2000, 36, 165–8).

Various classes of compounds containing inter alia a sulphonyl moiety are described in WO 01/64632, WO 00/43362, WO 96/35666, EP-A-0261688, EP-0304888, and U.S. Pat. Nos. 4,218,455 and 4,128,552, DE-A-3901735 and Fletcher et al, *J. Med. Chem.*, 2002, 45, 492–503. None of these publications, however, discloses or suggests the particular class of compounds provided by the present invention.

The compounds according to the present invention are potent and selective 5-HT$_{2A}$ receptor antagonists typically having a human 5-HT$_{2A}$ receptor binding affinity (K$_i$) of 100 nM or less, frequently of 50 nM or less and in preferred cases of 10 nM or less. The compounds of the invention may possess at least a 10-fold selective affinity, suitably at least a 20-fold selective affinity and preferably at least a 50-fold selective affinity, for the human 5-HT$_{2A}$ receptor relative to the human dopamine D$_2$ receptor. The compounds of this invention may possess at least a 10-fold selective affinity, suitably at least a 20-fold selective affinity and preferably at least a 50-fold selective affinity of the human 5-HT$_{2A}$ receptor relative to the IKr receptor. The compounds of this invention may possess at least a 10-fold selective affinity, suitably at least a 20-fold selective affinity and preferably at least a 50-fold selective affinity for the human 5-HT$_{2A}$ receptor relative to the human 5-HT$_{2C}$ receptor. Preferred compounds show selectivities of at least 100 fold relative to the human 5-HT$_{2C}$ receptor.

The present invention provides a compound of formula I:

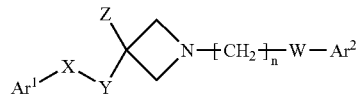

wherein n is 0, 1, 2 or 3;
W is CH$_2$, CO, CHF or CH(OH);
X is SO$_2$, SO, CO or CH(OH);
Y is CH$_2$, CHF or CF$_2$;
Z is H, F or OH;
Ar$^1$ is phenyl or heteroaryl, said heteroaryl having 5 or 6 ring atoms of which one, two or three are selected from N, O and S but not more than one of which is O or S, and said phenyl or heteroaryl optionally bearing up to 3 substituents selected from halogen, CN, NO$_2$, R$^1$, OR$^2$, COR$^2$, CO$_2$R$^2$, OCOR$^1$, SR$^2$, S(O)$_t$R$^1$ where t is 1 or 2, N(R$^2$)$_2$, CON(R$^2$)$_2$, NR$^2$COR$^1$ and SO$_2$N(R$^2$)$_2$;
Ar$^2$ is a mono- or bicyclic ring system of 5 to 10 ring atoms, of which 0 to 3 are selected from N, O and S, in which the ring bonded to W is aromatic or heteroaromatic, said ring system optionally bearing up to 3 substituents selected from halogen, CN, NO$_2$, R$^1$ and OR$^2$;
R$^1$ is a hydrocarbon group comprising up to 6 carbon atoms optionally bearing up to 5 fluorine substituents; and
R$^2$ is R$^1$ or H; or two R$^2$ groups attached to the same nitrogen atom may complete a morpholine or thiomorpholine ring, or a 5- or 6-membered heterocycle wherein the remaining ring atoms are selected from C and N to a maximum of 4 ring nitrogens in total;
or a pharmaceutically acceptable salt or hydrate thereof.

In a subset of the compounds of formula I, X is SO$_2$, CO or CH(OH);
Ar$^1$ is phenyl optionally bearing up to 3 substituents selected from halogen, CN, NO$_2$, R$^1$, OR$^2$, COR$^2$, CO$_2$R$^2$, OCOR$^1$, SR$^2$, S(O)$_t$R$^1$ where t is 1 or 2, N(R$^2$)$_2$, CON(R$^2$)$_2$, NR$^2$COR$^1$ and SO$_2$N(R$^2$)$_2$;
Ar$^2$ is phenyl or heteroaryl, said heteroaryl having 5 or 6 ring atoms of which one, two or three are selected from N, O and S but not more than one of which is O or S, said heteroaryl optionally being benzo-fused, and said phenyl or heteroaryl optionally bearing up to 3 substituents selected from halogen, CN, NO$_2$, R$^1$ and OR$^2$; and the remaining variables are as defined above.

Where a variable occurs more than once in formula I or in a substituent thereof, the individual occurrences of that variable are independent of each other, unless otherwise specified.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits.

As used herein, the expression "C$_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$ alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The expression "$C_{3-6}$cycloalkyl" as used herein refers to nonaromatic monocyclic hydrocarbon ring systems comprising from 3 to 6 ring atoms. Examples include cyclopropyl, cyclobutyl, cyclopentyl, cyclohexyl and cyclohexenyl.

The term "halogen" as used herein includes fluorine, chlorine, bromine and iodine, of which fluorine and chlorine are preferred.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulfonic acid, benzenesulfonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, the compound of formula I may exist as a zwitterion, or a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts. The compounds of formula I are typically in the form of the free base, the hydrochloride salt, the benzenesulfonate salt or the methanesulfonate salt.

When the compounds according to the invention have one or more asymmetric centres, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, n is 0, 1, 2 or 3 and W is $CH_2$, CO, CHF or CH(OH). In a preferred embodiment W is $CH_2$, CHF or CO, most preferably $CH_2$ or CO. When n is 0 W is preferably $CH_2$. When W is CHF or CH(OH), n is preferably 1. Specific examples of linkers represented by —[$CH_2$]$_n$—W— include $CH_2$, $CH_2CH_2$, $CH_2CO$, $CH_2CH_2CH_2CO$ and $CH_2CHF$.

X is $SO_2$, SO, CO or CH(OH), but in a preferred embodiment X is $SO_2$ or SO, and most preferably X is $SO_2$.

Y is $CH_2$, CHF or $CF_2$. In a particular embodiment Y is $CH_2$.

Z is H, F or OH. Preferably, Z is H or F.

$Ar^1$ is phenyl or heteroaryl which optionally bears up to 3 substituents as defined previously. Heteroaryl groups represented by $Ar^1$ comprise 5 or 6 ring atoms, 1, 2 or 3 of which are selected from N, O and S, with the proviso that not more than one is O or S. Suitable heteroaryl rings include pyridine, pyrimidine, thiophene, furan, thiazole, imidazole and triazole. Preferred heteroaryl rings represented by $Ar^1$ include pyridine, imidazole and thiazole. Typically, if more than one substituent is present on $Ar^1$, the substituents are halogen atoms, preferably fluorine atoms. Preferred substituents include halogen, CN, $R^1$, $OR^2$, $N(R^2)_2$ and $CON(R^2)_2$, where $R^1$ and $R^2$ are as defined previously. Typically $R^1$ is a non-aromatic hydrocarbon group optionally substituted with up to 5 (preferably up to 3) fluorine atoms. Preferably, the hydrocarbon group is a $C_{1-6}$alkyl, $C_{2-6}$alkenyl or $C_{3-6}$cycloalkyl group, most suitably a $C_{1-4}$alkyl group. Suitable identities for $R^1$ include methyl, ethyl, n-propyl, isopropyl, t-butyl, $CF_3$, $CHF_2$, $CH_2F$, allyl and cyclopropyl, of which methyl, ethyl and $CF_3$ are preferred. $R^2$ represents H or $R^1$, or two $R^2$ groups attached to the same nitrogen can complete a ring as defined previously. Examples of such rings include morpholine, thiomorpholine, pyrrolidine, piperidine, piperazine, imidazole and triazole. Examples of substituents on $Ar^1$ include halogen (especially Br, Cl or F), CN, methyl, $CF_3$, methoxy, $CF_3O$, $CONH_2$, morpholin-4-yl and 1,2,3-triazol-1-yl. Examples of groups represented by $Ar^1$ include phenyl, 4-fluorophenyl, 2,4-difluorophenyl, 2-fluorophenyl, 3-bromophenyl, 4-cyanophenyl, 1-methylimidazol-2-yl, thiazol-2-yl and 4-pyridyl. Particularly preferred examples of groups represented by $Ar^1$ include 4-fluorophenyl and 2,4-difluorophenyl.

$Ar^2$ represents a mono- or bicyclic ring system of 5 to 10 members as defined previously. Monocyclic ring systems represented by $Ar^2$ are aromatic or heteroaromatic, and in bicyclic ring systems represented by $Ar^2$ at least the ring bonded to W is aromatic or heteroaromatic. The definition of $Ar^2$ therefore encompasses phenyl and 5- or 6-membered heteroaryl groups, any of which is optionally fused to a second ring providing a total of up to 10 ring atoms. Said second ring may be carbocyclic or heterocyclic, provided the total number of heteroatoms in the ring system does not exceed 3. Preferably, no individual ring comprises more than 2 heteroatoms. Said second ring may be saturated, partially unsaturated or aromatic. Examples of suitable ring systems, represented by $Ar^2$, include phenyl, naphthyl, and 5-or 6-membered heteroaryl groups such as furan, pyrrole, thiophene, oxazole, isoxazole, thiazole, isothiazole, imidazole, pyridine, pyrimidine and their benzo-fused and tetrahydrobenzo-fused derivatives. Further suitable ring systems include fused systems in which both rings are heteroaryl, such as thieno[2.3-b]thienyl. Typically, if more than one substituent is present on $Ar^2$, the substituents are halogen atoms, preferably fluorine atoms, or alkyl groups. Preferred substituents include halogen (especially F, Br or Cl), OH, CN, $C_{1-4}$alkyl (especially methyl) and $CF_3$. When $Ar^2$ is bicyclic, said optional substituent(s) may be located on either ring or both rings. Specific examples of groups represented by $Ar^2$ include 4-fluorophenyl, 2,4-difluorophenyl, 4-fluoro-2-methylphenyl, 2-chlorophenyl, 6-fluorobenzothiophene-3-yl, benzothiazol-2-yl, 6-fluorobenzisothiazol-3-yl, 6-fluorobenzisoxazol-3-yl, 4-chlorophenyl, 2-chloro-4-fluorophenyl, 3,4-difluorophenyl, 4-bromophenyl, phenyl, 2-bromo-4-fluorophenyl, isoquinolin-1-yl, 6-chlorobenzothiophen-3-yl, 4,5,6,7-tetrahydrobenzothiophen-3-yl, thieno[2.3-b]thien-3-yl, 2-fluorobenzothiophen-3-yl, 4-fluoro-2-hydroxyphenyl, thiophen-3-yl, thiophen-2-yl, benzisothiazol-3-yl, 1-naphthyl, 2-naphthyl, 2,4-dimethylphenyl and 4-fluoro-2-methylphenyl.

In a particular embodiment, when $Ar^2$ is a fused bicyclic group, W is $CH_2$ and n is 0.

A subset of the compounds of the invention is defined by formula II:

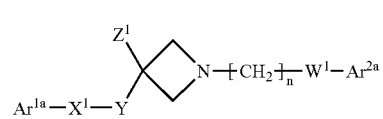

II and the pharmaceutically acceptable salts and hydrates thereof; wherein:

$W^1$ is $CH_2$ or CO;
$Z^1$ is H or F;
$X^1$ is SO or $SO_2$;
$Ar^{1a}$ is phenyl bearing up to 2 substituents selected from F, Cl, Br, CN, methyl, $CF_3$, methoxy, $CF_3O$ and $CONH_2$;
$Ar^{2a}$ is phenyl or 5- or 6-membered heteroaryl comprising up to 2 heteroatoms selected from O, N and S, optionally bearing up to 2 substituents selected from F, Cl, Br, OH and $C_{1-4}$ alkyl;
and Y and n have the same meanings and preferred identities as before.

Within this subset, n is preferably 1.
Within this subset, $X^1$ is preferably $SO_2$.
Within this subset, $Z^1$ is preferably H.
Within this subset, $Ar^{1a}$ is preferably phenyl which bears up to 2 substituents selected from F, Cl, Br and CN.
Within this subset $Ar^{2a}$ is preferably phenyl which bears up to 2 substituents selected from F, Cl, Br, OH and methyl.

In a particular embodiment, $Ar^{1a}$ is selected from 4-fluorophenyl, 2,4-difluorophenyl, 2-fluorophenyl, 3-bromophenyl and 4-cyanophenyl; and $Ar^{2a}$ is selected from 4-fluorophenyl, 2,4-difluorophenyl, 4-fluoro-2-methylphenyl, 2-chlorophenyl, 4-chlorophenyl, 2-chloro-4-fluorophenyl, 3,4-difluorophenyl, 4-bromophenyl, 2-bromo-4-fluorophenyl, thiophen-2-yl, thiophen-3-yl, 2,4-dimethylphenyl, 4-fluoro-2-methylphenyl and 4-fluoro-2-hydroxyphenyl.

Another subset of the compounds of the invention is defined by formula III:

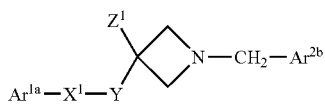

III and the pharmaceutically acceptable salts and hydrates thereof, wherein:
$Ar^{2b}$ represents a 5- or 6-membered heteroaryl ring comprising up to two heteroatoms selected from N, O and S which is fused to a benzene ring, said heteroaryl ring and fused benzene ring together optionally bearing up to 2 substituents selected from F, Cl, Br, OH and $C_{1-4}$alkyl;
and $Ar^{1a}$, $X^1$, Y and $Z^1$ have the same definitions and preferred identities as before.

Within this subset, Y is preferably $CH_2$.
$Ar^{2b}$ preferably represents quinolyl, isoquinolyl, benzothiophenyl, benzisothiazolyl or benisoxazolyl optionally bearing up to 2 substituents slected from F, Cl, Br, OH and methyl.

In a particular embodiment, $Ar^{2b}$ is selected from 6-fluorobenzothiophen-3-yl, benzothiazol-2-yl, 6-fluorobenzothiazol-3-yl, 6-fluorobenzisoxazol-3-yl, isoquinolin-1-yl, 6-chlorobenzothiophen-3-yl, 2-fluorobenzothiophen-3-yl and benzisothiazol-3-yl.

Specific examples of compounds in accordance with the invention include those exemplified hereinafter and pharmaceutically acceptable salts and hydrates thereof.

The compounds of the present invention have an activity as antagonists of the human $5\text{-HT}_{2A}$ receptor and hence find use in the treatment or prevention of disorders mediated by $5\text{-HT}_{2A}$ receptor activity.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

The present invention also provides a compound of formula I or a pharmaceutically acceptable salt or hydrate thereof for use in a method of treatment of the human body. Preferably the treatment is for a condition mediated by $5\text{-HT}_{2A}$ receptor activity.

The present invention further provides the use of a compound of formula I or a pharmaceutically acceptable salt or hydrate thereof in the manufacture of a medicament for treating or preventing a condition mediated by $5\text{-HT}_{2A}$ receptor activity in humans.

Also disclosed is a method of treatment of a human subject suffering from or prone to a condition mediated by $5\text{-HT}_{2A}$ receptor activity which comprises administering to that subject an effective amount of a compound according to formula I or a pharmaceutically acceptable salt or hydrate thereof.

In one aspect of the invention, the condition mediated by $5\text{-HT}_{2A}$ receptor activity is a sleep disorder, in particular insomnia. In a further aspect of the invention, the condition mediated by 5-HT$_{2A}$ receptor activity is selected from psychotic disorders (such as schizophrenia), depression, anxiety, panic disorder, obsessive-compulsive disorder, pain, eating disorders (such as anorexia nervosa), dependency or acute toxicity associated with narcotic agents such as LSD or MDMA, and hot flushes associated with the menopause.

In the treatment envisaged herein, for example of insomnia or schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day but preferably once per day, for example before going to bed.

If desired, the compounds according to this invention may be co-administered with another sleep inducing or anti-schizophrenic or anxiolytic medicament. Such co-administration may be desirable where a patient is already established on sleep inducing or anti-schizophrenic or anxiolytic treatment regime involving other conventional medicaments. In particular, for the treatment of sleep disorders, the compounds of the invention may be co-administered with a GABA$_A$ receptor agonist such as gaboxadol, or with a short term and/or rapid-onset hypnotic such as zolpidem, or a benzodiazepine, a barbiturate, a prokineticin modulator, an antihistamine, trazodone, or derivative of trazodone as disclosed in WO 03/068148.

The compounds of formula I may be obtained by reaction of compounds of formula (1a) with compounds of formula (2):

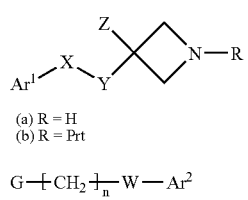

(1)

(a) R = H
(b) R = Prt $$G\text{---}(CH_2)_n\text{---}W\text{---}Ar^2 \quad (2)$$

wherein G is a leaving group such as mesylate, tosylate or halide (especially bromide) and n, W, X, Y, Z, Ar$^1$ and Ar$^2$ have the same meanings as before. The reaction takes place under typical alkylation conditions, e.g. in a solvent such as DMF, acetonitrile, acetone, or 2-butanone at ambient or moderately elevated temperatures (e.g. about 70–90° C.), in the presence of a base such as potassium carbonate.

Alternatively, compounds of formula I in which n is 1 or more may be formed by reacting amines (1a) with aldehydes (3):

$$Ar^2\text{---}W\text{---}(CH_2)_m\text{---}CHO \quad (3)$$

where m is 0, 1 or 2 and W and Ar$^2$ have the same meanings as before. The reaction takes place in the presence of sodium cyanoborohydride in alcoholic solution (eg methanol) at ambient temperature.

The amines (1a) may be preformed or formed in situ from compounds (1b) where Prt is a protecting group. Preferred protecting groups include diphenylmethyl (which may be removed by hydrogenation over a Pd(OH)$_2$ catalyst) and t-butoxycarbonyl (BOC) (which may be removed by treatment with acid, eg trifluoroacetic acid or HCl in aqueous dioxan).

Compounds (1b) in which X is SO or SO$_2$ and Y is CH$_2$ are obtainable by oxidation of thioethers (4):

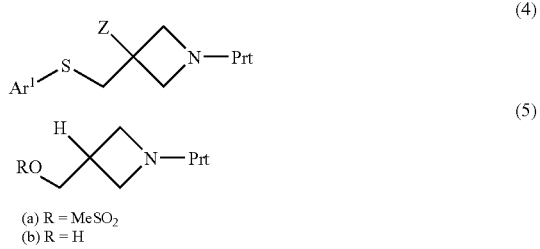

(a) R = MeSO$_2$
(b) R = H where Z and Ar$^1$ have the same meanings as before. Suitable oxidants include Oxone™, in methanol at 0° C. to ambient temperature. Use of one equivalent of the oxidant provides sulfoxides (X=SO) and use of two or more equivalents provides sulfones (X=SO$_2$). Other suitable oxidants include m-chloroperoxybenzoic acid and osmium tetroxide.

Thioethers (4) in which Z is H are obtainable by treatment of mesylates (5a) with thiophenols Ar$^1$SH (eg in refluxing acetonitrile in the presence of potassium carbonate), where Ar$^1$ has the same meaning as before. Mesylates (5a) are obtained by treatment of hydroxymethyl derivatives (5b) with methanesulfonyl chloride in an inert solvent such as dichloromethane in the presence of base such as triethylamine.

Thioethers (4) in which Z is OH are obtainable by reaction of epoxide (6) with thiophenols Ar$^1$SH:

where Ar$^1$ has the same meaning as before, and Prt is preferably diphenylmethyl. The reaction takes place in the presence of strong base such as sodium hydride in an aprotic solvent such as THF at about 0° C. The synthesis of epoxide (6) (Prt=diphenylmethyl) is described in WO97/42189.

Thioethers (4) in which Z is F are obtainable by reaction of the thioethers (4) in which Z is OH with (diethylamino) sulfur trifluoride, for example in dichloromethane at –10° C. to ambient temperature.

Compounds (1b) in which Y is CHF or CF$_2$ are obtainable from the corresponding compounds in which Y is CH$_2$ by fluorination with N-fluorobenzenesulfonimide, for example in THF at –78° C. to ambient temperature. Typically, a mixture of mono- and di-fluorinated products is obtained which may be separated by chromatography. In this process, the protecting group Prt is preferably BOC.

Compounds (1b) in which X is CO, Y is CH$_2$ and Z is H may be obtained by treatment of N,N-dimethoxyacetamides (7) with Ar$^1$—MgHal:

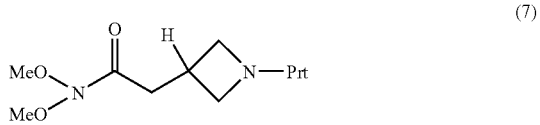

where Hal is Cl, Br or I and Ar$^1$ and Prt have the same meanings as before. The reaction takes place at –78° C. to ambient temperature in an aprotic solvent such as THF under nitrogen. Compounds (7) are obtainable by treatment of an alkyl ester of an N-protected azetidin-3-yl acetic acid with N,O-dimethylhydroxylamine, the reaction taking place in THF at −20° in the presence of a Grignard reagent such as isopropylmagnesium chloride.

An alternative route to compounds (1b) in which X is $SO_2$, Y is $CH_2$ and Z is H involves reaction of mesylates (5a) with $Ar^1$—$SO_2^-M^+$, where M is an alkali metal (preferably Na) and $Ar^1$ has the same meaning as before. The reaction takes place in DMF at about 80° C. in the presence of sodium iodide. The desired sulfone is produced along with a sulfinate ester by-product, from which it may be separated by conventional chromatographic techniques.

It will be apparent to those skilled in the art that in many cases the sequences of steps outlined above may be carried out in a different order. For example, N-alkylation of the azetidine ring may be performed prior to the construction of the $Ar^1$—X—Y— moiety.

In cases where any of the substituents in any of the compounds require protection during any of the preceding reactions this may be effected in conventional manner. Alternatively there may be instances where a particular substituent may be introduced after the above reactions are performed. Thus for example where a nitrile is required as a substituent it may be introduced by replacing a bromine atom, for example reacting the appropriate bromo-compound of the formula (I) in an anhydrous solvent such as dimethylformamide with zinc cyanide in the presence of tetrakis(triphenylphosphine)palladium with heating, for example to 85–95° C. Introduction of a nitrile or heterocycle can be also performed by replacement of fluorine by nucleophilic displacement, for example by heating with NaCN or a triazole in DMSO. Other modifications of substituents can be carried out by conventional art methods, for example as set out in WO 00/43362 or Fletcher et al, *J. Med. Chem.*, 2002, 45, 492–503.

Where they are not commercially available, the starting materials and reagents used in the above-described synthetic schemes may be prepared by conventional means.

It will be appreciated that where more than one isomer can be obtained from a reaction the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid or di-p-toluoyl-L-tartaric acid, followed by fractional crystallization and regeneration of the free base. The novel compounds may also be resolved by formation of diastereomeric esters or amides, followed by chromatographic separation and removal of the chiral auxiliary. Alternatively, such techniques may be carried out on racemic synthetic precursors of the compounds of interest.

Compounds were tested at the 5-$HT_{2A}$ receptor as well as IKr and 5-$HT_{2c}$ receptor using the methodology described in Fletcher et al, *J. Med. Chem.*, 2002, 45, 492–503.

The following examples illustrate the invention.

EXAMPLE 1

1-[2-(2,4-Difluorophenyl)ethyl]-3-{[(4-fluorophenyl)sulfonyl]methyl}azetidine

Step 1: [1-(Diphenylmethyl)azetidin-3-yl]methyl methanesulfonate

A solution of 1-(diphenylmethyl)-3-(hydroxymethyl) azetidine (1 g, 3.9 mmol) [prepared by reduction of 1-(diphenylmethyl)azetidine-3-carboxylic acid (CAS No.: 36476-87-6) using $LiAlH_4$ in refluxing THF] and $Et_3N$ (0.71 mL, 5.1 mmol) in THF (30 mL) was treated with methanesulfonyl chloride (0.36 mL, 4.7 mmol) and stirred for 2 h at room temperature. The precipitate was removed by filtration and washed with THF. The liquors were evaporated and the residue partitioned between water and DCM. The DCM layer was separated and the aqueous re-extracted. The combined organics were washed with brine, dried ($Na_2SO_4$), filtered and evaporated. The residue was triturated with isohexane, the solid then isolated by filtration and dried to give the title compound as an orange solid (1.1 g, 84%). m/z ($ES^+$) 332 $(M+H)^+$.

Step 2: 1-(Diphenylmethyl)-3-{[(4-fluorophenyl)thio]methyl}azetidine

A solution of the foregoing mesylate (0.8 g, 2.4 mmol) in MeCN (30 mL) was degassed with nitrogen. 4-Fluorothiophenol (0.51 mL, 4.8 mmol) and powdered $K_2CO_3$ (1.3 g, 9.6 mmol) were then added and the reaction heated at reflux for 1 h. The cooled mixture was transferred to a separating funnel and diluted with DCM (100 mL) and water. The organic layer was separated and the aqueous re-extracted. The combined organics were dried ($Na_2SO_4$), filtered and evaporated. The residue was purified by silica column chromatography eluting with 5% EtOAc/isohexane then 10% EtOAc/isohexane to give the title compound as a colourless oil (0.86 g, 97%). m/z ($ES^+$) 364 $(M+H)^+$.

Step 3: 1-(Diphenylmethyl)-3-{[(4-fluorophenyl)sulfonyl]methyl}azetidine

A mixture of the foregoing sulfide (1 g, 2.75 mmol) and oxone® (3.4 g, 5.5 mmol) in MeOH (50 mL) was stirred for 8 days. DCM (250 mL) and saturated $NaHCO_3$ solution were added and stirred for 10 min. The organic layer was separated and the aqueous re-extracted. The combined organics were washed with brine, dried ($Na_2SO_4$), filtered and evaporated. The residue was purified on a silica column eluting DCM then 5% EtOAc/DCM. The title compound was collected as a colourless gum (0.7 g, 64%). m/z ($ES^+$) 396 $(M+H)^+$.

Step 3a: 1-(Diphenylmethyl)-3-{[(4-fluorophenyl)sulfonyl]methyl}azetidine (Alternative route)

[1-(Diphenylmethyl)azetidin-3-yl]methyl methanesulfonate [Step 1] (3.15 g, 9.50 mmol), sodium 4-fluorobenzenesulfinate (2.65 g, 14.3 mmol) and sodium iodide (2.18 g, 14.5 mmol) were combined in dimethylformamide (50 mL). The mixture was stirred at 80° C. (oil bath temperature) under nitrogen for 1.5 h. The solution was allowed to cool to room temperature, poured into water (500 mL) and extracted with ethyl acetate (2×200 mL). The organic extracts were washed with brine (200 mL), combined, dried ($MgSO_4$) and concentrated in vacuo. The residue was purified by flash chromatography, eluting with 5–20% ethyl acetate in dichloromethane, to afford an oil which crystallised on standing. Recrystallisation from ethyl acetate/isohexane gave the title compound, identical to the product obtained via steps 2 and 3.

Step 4: 3-{[(4-Fluorophenyl)sulfonyl]methyl}azetidine hydrochloride

The foregoing sulfone (0.7 g, 1.8 mmol), EtOH (60 mL), 5N HCl (0.5 mL, 2.5 mmol), 20% Pd(OH)$_2$ on carbon (0.6 g) and water (5 mL) were combined and shaken for 2 h under 50 psi of hydrogen on a Parr machine. The catalyst was removed by filtration and the filtrate evaporated. The residue was triturated with ether and filtered to collect the title compound as a white solid (375 mg, 80%). m/z (ES$^+$) 230 (M+H)$^+$.

Step 5: 1-[2-(2,4-Difluorophenyl)ethyl]-3-{[(4fluorophenyl)sulfonyl]methyl}azetidine The foregoing azetidine hydrochloride (115 mg, 0.43 mmol), K$_2$CO$_3$ (176 mg, 1.28 mmol), 2,4-difluorophenethyl bromide (140 mg, 0.64 mmol) and DMF (5 mL) were combined and heated at 70° C. for 12 h. The mixture was evaporated by forming an azeotrope with xylene and the resultant residue partitioned between DCM and water. The DCM layer was separated and the aqueous re-extracted. The combined organics were washed with brine, dried (Na$_2$SO$_4$), filtered and evaporated. The residue was purified using silica column chromatography eluting 0.5% MeOH/DCM then 2% MeOH/DCM. Further purification was carried out using preparative HPLC with UV detection using 20–95% gradient MeCN using 0.1% TFA in the aqueous phase. The MeCN was evaporated from the product fractions, the aqueous made basic and extracted with EtOAc. The combined organics were washed with brine, dried (Na$_2$SO$_4$), filtered and evaporated to give a colourless gum (66 mg, 41%). $^1$H NMR (400 MHz, CDCl$_3$) δ 2.82 (3H, m), 3.35 (2H, d, J=6.4 Hz), 3.40 (2H, m), 6.72–6.80 (2H, m), 7.08–7.12 (1H, m), 7.24 (2H, t, J=8.7 Hz), 7.88–7.91 (2H, dd, J=8.7 and 5.1 Hz). m/z (ES$^+$) 370 (M+H)$^+$.

EXAMPLE 2

1-(4-Fluorophenyl)-2-(3-{[(4-fluorophenyl)sulfonyl]methyl}azetidin-1-yl)ethanone A mixture of 3-{[(4-fluorophenyl)sulfonyl]methyl}azetidine hydrochloride (75 mg, 0.28 mmol) in MeCN (5 mL) was treated with Et$_3$N (97 µL, 0.7 mmol) and 2-bromo-4'-fluorophenylacetophenone (68 mg, 0.31 mmol) and stirred for 30 min at room temperature. The reaction was evaporated and the residue dissolved in DCM and purified using silica chromatography. The column was eluted with 1% MeOH/DCM to give the title compound as a white solid (70 mg, 68%). $^1$H NMR (500 MHz, CDCl$_3$) δ 2.94–2.99 (1H, m), 3.10 (2H, t, J=7.4 Hz), 3.42 (2H, d, J=7.4 Hz), 3.62 (2H, t, J=7.4 Hz), 3.87 (2H, s), 7.12 (2H, t, J=8.8 Hz), 7.25 (2H, t, J=8.6 Hz), 7.90–7.94 (4H, m). m/z (ES$^+$) 366 (M+H)$^+$.

EXAMPLE 3

1-(4-Fluorophenyl)-4-(3-{[(4-fluorophenyl)sulfonyl]methyl}azetidin-1-yl)butan-1-one hydrochloride A stirred mixture of 3-{[(4-fluorophenyl)sulfonyl]methyl}azetidine hydrochloride (150 mg, 0.56 mmol), 2-butanone (5 mL), potassium carbonate (0.25 g, 1.81 mmol), sodium iodide (20 mg, 0.13 mmol) and 4-chloro-1-(4-fluorophenyl)butan-1-one (115 µL, 0.68 mmol) was heated at reflux for 5 h under an inert atmosphere. The cooled reaction mixture was partitioned between EtOAc and water. The EtOAc extracts were washed with water and saturated brine then dried (MgSO$_4$), filtered and concentrated in vacuo. The resultant material was purified by column chromatography on silica eluted with a gradient of 0–15% MeOH-EtOAc to give the free base. This was dissolved in EtOAc and treated with 1M HCl in diethyl ether. The solvents was removed in vacuo to give 1-(4-fluorophenyl)-4-(3-{[(4-fluorophenyl)sulfonyl]methyl}azetidin-1-yl)butan-1-one hydrochloride as a white solid (16 mg). $^1$H NMR (400 MHz, CD$_3$OD) δ 1.90–1.99 (2H, m), 3.17 (2H, t, J=6.6 Hz), 3.25–3.35 (3H, m), 3.68 (2H, d, J=7.3 Hz), 4.0–4.2 (2H, br s), 4.2–4.4 (2H, br s), 7.20–7.27 (2H, m), 7.39–7.46 (2H, m), 7.98–8.04 (2H, m), 8.05–8.10 (2H, m). m/z (ES$^+$) 394 (M+H)$^+$.

EXAMPLE 4

2-(3-{[(2,4-Difluorophenyl)sulfonyl]methyl}azetidin-1-yl)-1-(4-fluorophenyl)ethanone hydrochloride Step 1: 3-{[(2,4-Difluorophenyl)sulfonyl]methyl}azetidine hydrochloride Prepared as described in Example 1, Steps 1–4 using 2,4-difluorothiophenol in Step 2, and isolated as a colourless solid (264 mg). $^1$H NMR (500 MHz, d$_6$-DMSO) δ 3.01–3.11 (1H, m), 3.75–3.85 (2H, m), 3.88–3.96 (3H, m), 7.39–7.42 (1H, m), 7.69–7.73 (1H, m), 7.89–7.93 (1H, m), 8.98–9.15 (2H, br s). m/z (ES$^+$) 248 (M+H)$^+$.

Step 2: 2-(3-{[(2,4-Difluorophenyl)sulfonyl]methyl}azetidin-1-yl)-1-(4-fluorophenyl)ethanone hydrochloride 3-{[(2,4-Difluorophenyl)sulfonyl]methyl}azetidine hydrochloride (60 mg, 0.21 mmol) and 2-bromo-1-(4-fluorophenyl)ethanone (52 mg, 0.23 mmol) were stirred together at room temperature with K$_2$CO$_3$ (90 mg, 0.65 mmol) in DMF (3 mL) under an inert atmosphere. Water was added to the mixture after 5.5 h and the mixture was then extracted with EtOAc. The organic extracts were washed with water and saturated brine then dried (MgSO$_4$), filtered and concentrated in vacuo. The resultant material was purified using preparative thin layer chromatography on silica eluted with 50% EtOAc-isohexane to give the free base. This was then dissolved in EtOAc and treated with 1M HCl in diethyl ether. The solids was filtered off and dried in vacuo to give 2-(3-{[(2,4-difluorophenyl)sulfonyl]methyl}azetidin-1-yl)-1-(4-fluorophenyl)ethanone hydrochloride as a colourless solid (12 mg). $^1$H NMR (500 MHz, d$_6$-DMSO) δ 3.09–3.19 (2H, m), 3.95 (2H, d, J=7.1 Hz), 4.01–4.16 (2H, br s), 4.17–4.29 (2H, m), 5.06 (2H, s), 7.40–7.47 (3H, m), 7.70–7.75 (1H, m), 7.91–7.94 (1H, m), 7.99–8.02 (2H, m), 10.72 (1H, br s). m/z (ES$^+$) 384 (M+H)$^+$.

EXAMPLE 5

2-(3-Fluoro-3-{[(4-fluorophenyl)sulfonyl]methyl}azetidin-1-yl)-1-(4-fluorophenyl)ethanone hydrochloride Step 1: 1-(Diphenylmethyl)-3-{[(4-fluorophenyl)thio]methyl}azetidin-3-ol Sodium hydride (0.128 g of a 60% dispersion in mineral oil, 3.2 mmol) was added to a solution of 4-fluorobenzenethiol (0.29 mL, 2.7 mmol) in THF (10 mL). The resulting mixture was stirred at room temperature for 10 min and then cooled to 0° C. A solution of 5-(diphenylmethyl)-1-oxa-5-azaspiro[2.3]hexane [prepared by the method of J. L. Castro Pineiro et al. WO 97/42189] (0.68 g, 2.71 mmol) in THF (8 mL) was added and the resulting mixture stirred at −1° C. for 40 min then at room temperature overnight. The reaction mixture was poured into water (200 mL) and extracted with EtOAc (100 mL then 50 mL). The organic extracts were washed with saturated brine (100 mL), combined, dried (MgSO$_4$) and concentrated. The residue was purified by flash silica chromatography, eluting with 25% EtOAc/isohexane, to give the title product as an oil (0.82 g, 80%). $^1$H NMR (400 MHz, CDCl$_3$) δ 2.67 (1H, s), 2.94–2.96 (2H, m), 3.18–3.20 (2H, m), 3.43 (2H, s), 4.34 (1H, s), 6.96–7.02 (2H, m), 7.15–7.19 (2H, m), 7.23–7.26 (4H, m), 7.34–7.36 (4H, m), 7.41–7.46 (2H, m). (376 MHz, CDCl$_3$) δ$_F$ −115.2. m/z (ES$^+$) 380 (M+H)$^+$.

Step 2: 1-(Diphenylmethyl)-3-fluoro-3-{[(4-fluorophenyl)sulfonyl]methyl}azetidine (Diethylamino)sulfur trifluoride (75 mL, 0.57 mmol) was added dropwise to a solution of 1-(diphenylmethyl)-3-{[(4-fluorophenyl)thio]methyl}azetidin-3-ol (171 mg, 0.451 mmol) in DCM (5 mL) at −10° C. The resulting solution was stirred at −10° C. under nitrogen for 20 min, the cooling bath removed and the mixture stirred for a further 30 min. The reaction was quenched by the addition of saturated aqueous sodium hydrogen carbonate (5 mL), the organic layer and the aqueous phase extracted with DCM (2×5 mL). The combined organic extracts were dried (MgSO$_4$) and evaporated. The residue was purified by flash silica chromatography, eluting with 3:1 DCM/isohexane then DCM to give an oil (136 mg). A portion of this material (129 mg) was dissolved in methanol (5 mL), the solution cooled to 0° C. and treated with oxone® (464 mg, 0.75 mmol). The resulting mixture was stirred at 0° C. for 1 h then at room temperature overnight. The reaction mixture was poured into saturated aqueous sodium hydrogen carbonate and extracted with DCM (40 mL then 2×20 mL). The combined organic extracts were dried (MgSO$_4$) and evaporated. The residue was purified by preparative thin layer chromatography, eluting with 3:1 DCM/isohexane to afford the title compound as an oil (67 mg, 38%). $^1$H NMR (500 MHz, CDCl$_3$) δ 3.23 (2H, dd, J=22.5 and 10.3 Hz), 3.54–3.59 (2H, m), 3.76 (2H, d, J=21 Hz), 4.37 (1H, s), 7.17–7.22 (4H, m), 7.25–7.28 (4H, m), 7.36–7.38 (4H, m), 7.90 (2H, dd, J=8.8 and 5.1 Hz). (376 MHz, CDCl$_3$) δ$_F$ −103.6, −146.5. m/z (ES$^+$) 414 (M+H)$^+$.

Step 3: 2-(3-Fluoro-3-{[(4-fluorophenyl)sulfonyl]methyl}azetidin-1-yl)-1-(4-fluorophenyl)ethanone hydrochloride 1M HCl in diethyl ether (0.18 mL, 0.18 mmol) and palladium hydroxide on carbon (26.1 mg; 20 wt. %) were added to a solution of 1-(diphenylmethyl)-3-fluoro-3-{[(4-fluorophenyl)sulfonyl]methyl}azetidine (57 mg, 0.138 mmol) in MeOH (10 mL). The resulting mixture was hydrogenated on Parr apparatus, 50 psi max., for 2.5 h. The mixture was filtered and concentrated in vacuo. The residual solid was washed twice with diethyl ether. The resulting solid was dissolved in DMF (2 mL) and treated with potassium carbonate (64 mg, 0.46 mmol) then 2-bromo-4'-fluoroacetophenone (34 mg, 0.156 mmol). The reaction mixture was stirred at room temperature for 1.5 h, diluted with water (20 mL) and extracted with EtOAc (2×10 mL). The combined organic extracts were washed with saturated brine (10 mL), dried (MgSO$_4$) and concentrated. The residue was purified by preparative thin layer chromatography, eluting with 1:1 EtOAc/isohexane, to afford an oil (20 mg, 38%). This material was dissolved in EtOAc and treated with 1M HCl in diethyl ether (0.067 mL). The mixture was diluted with diethyl ether and triturated to give a crystalline solid which was collected under suction to afford the title compound (21 mg). $^1$H NMR (500 MHz, d$_6$-DMSO) δ 4.44 (2H, d, J=22 Hz), 4.51–4.57 (2H, m), 4.65–4.71 (2H, m), 5.20 (1H, s), 7.45–7.49 (2H, m), 7.52–7.56 (2H, m), 8.00–8.03 (4H, m). m/z (ES$^+$) 384 (M+H)$^+$.

EXAMPLE 6

1-[2-(2,4-Difluorophenyl)ethyl]-3-{fluoro[(4-fluorophenyl)sulfonyl]methyl}azetidine hydrochloride Step 1: tert-Butyl 3-{[(4-fluorophenyl)sulfonyl]methyl}azetidine-1-carboxylate Triethylamine (0.12 mL, 0.86 mmol) was added to a suspension of 3-{[(4-fluorophenyl)sulfonyl]methyl}azetidine hydrochloride [Example 1, Step 4] (205 mg, 0.77 mmol) in DCM (5 mL), the resulting mixture was stirred at room temperature for 5 min then a solution of di-tert-butyl dicarbonate (176 mg, 0.81 mmol) in DCM (2.5 mL) was added. The reaction mixture was stirred for 2.5 h then washed with 5% aqueous citric acid (10 mL) and saturated aqueous sodium hydrogen carbonate (10 mL). The aqueous washes were extracted with DCM (2×5 mL), the combined organics dried (MgSO$_4$) and concentrated to an oil. Diethyl ether and isohexane were added and the mixture evaporated to give the title compound as a white solid (241 mg, 95%). $^1$H NMR (500 MHz, CDCl$_3$) δ 1.41 (9H, s), 2.92–3.01 (1H, m), 3.37 (2H, d, J=7.6 Hz), 3.64 (2H, br s), 4.40 (2H, t, J=8.6 Hz), 7.24–7.28 (2H, m), 7.89–7.92 (2H, m).

Step 2: tert-Butyl 3-{fluoro[(4-fluorophenyl)sulfonyl]methyl}azetidine-1-carboxylate and tert-butyl 3-{difluoro[(4-fluorophenyl)sulfonyl]methyl}azetidine-1-carboxylate n-Butyllithium (0.53 mL of a 1.6M solution in hexanes, 0.85 mmol) was added to a solution of tert-butyl 3-{[(4-fluorophenyl)sulfonyl]methyl}azetidine-1-carboxylate (227 mg, 0.69 mmol) in THF (5 mL) cooled to −78° C. The reaction mixture was stirred at −78° C. for 30 min and treated with N-fluorobenzenesulfonimide (269 mg, 0.85 mmol) in THF (3 mL). The reaction mixture was stirred at −78° C. for 5 min, the cooling bath was removed allowing the reaction mixture to warm to room temperature over 10 min and then stirred for a further hour. The reaction mixture was poured into water (40 mL) and extracted with EtOAc (2×20 mL). The extracts were washed with saturated brine (20 mL), combined, dried (MgSO$_4$) and evaporated. The residue was dissolved in THF (5 mL), cooled to −78° C. and treated with n-butyllithium, (0.56 mL of a 1.6M solution in hexanes, 0.90 mmol). The resulting mixture was stirred at −78° C. for 20 min and then treated with N-fluorobenzenesulfonimide (275 mg, 0.87 mmol) in THF (3 mL). The reaction mixture was stirred at −78° C. for 5 min, the cooling bath was removed allowing the reaction mixture to warm to room temperature over 10 min and then stirred for a further 2 h. The reaction mixture was poured into water (40 mL) and extracted with EtOAc (2×20 mL). The extracts were washed with saturated brine (20 mL), combined, dried (MgSO$_4$) and evaporated. The residue was purified by flash silica chromatography, eluting with 2.5% to 10% EtOAc/DCM to give tert-butyl 3-{difluoro[(4-fluorophenyl)sulfonyl]methyl}azetidine-1-carboxylate (64 mg, 25%). $^1$H NMR (500 MHz, CDCl$_3$) δ 1.43 (9H, s), 3.22 (2H, br s), 3.54–3.65 (1H, m), 4.13–4.15 (2H, m), 7.31–7.34 (2H, m), 7.99–8.02 (2H, m); as the first eluting product and then tert-butyl 3-{fluoro[(4-fluorophenyl)sulfonyl]methyl}azetidine-1-carboxylate (88 mg, 37%). $^1$H NMR (500 MHz, CDCl$_3$) δ 1.44 (9H, s), 3.24–3.36 (1H, m), 3.96 (1H, br s), 3.99–4.02 (2H, m), 4.15 (1H, dt, J=9 and 1.5 Hz), 5.29 (1H, dd, J=48 and 6 Hz), 7.28–7.32 (2H, m), 7.95–7.97 (2H, m).

Step 3: 1-[2-(2,4-Difluorophenyl)ethyl]-3-{fluoro[(4-fluorophenyl)sulfonyl]methyl}azetidine hydrochloride 4M HCl in dioxane (4 mL) was added to tert-butyl 3-{fluoro[(4-fluorophenyl)sulfonyl]methyl}azetidine-1-carboxylate (84 mg, 0.24 mmol) and the resulting solution stirred at room temperature for 1.3 h. The solution was evaporated, diethyl ether added and the mixture re-evaporated to give a foam (73 mg). This material was dissolved in MeOH (3 mL) and a solution of (2,4-difluorophenyl)acetaldehyde (45 mg, 0.29 mmol) in toluene (0.9 mL) added, followed by sodium cyanoborohydride (20 mg, 0.32 mmol). The resulting mixture was stirred at room temperature for 2 h, after which time a further portion of sodium cyanoborohydride (10 mg, 0.16 mmol) was added. The reaction mixture was stirred for 1.3 h, diluted with 0.5M aqueous sodium hydroxide solution (20 mL) and extracted with EtOAc (2×10 mL). The extracts were washed with saturated brine (10 mL), combined, dried (MgSO$_4$) and evaporated. The residue was purified by flash silica chromatography, eluting with 1:1 EtOAc/isohexane then EtOAc to afford an oil. This material was dissolved in EtOAc, the resulting solution heated and treated with 1M HCl in diethyl ether (0.16 mL). The mixture was evaporated and the residual solid recrystallised from EtOAc to give the title product (32 mg, 31%). $^1$H NMR (400 MHz, CD$_3$OD) δ 2.95 (2H, t, J=7.7 Hz), 3.48–3.51 (2H, m), 3.73–3.86 (1H, m), 4.24–4.43 (4H, m), 5.80 (1H, dd, J=47.5 and 3.6 Hz), 6.96–7.03 (2H, m), 7.36–7.41 (1H, m), 7.47 (2H, t, J=8.7 Hz), 8.02–8.06 (2H, m). m/z (ES$^+$) 388 (M+H)$^+$.

EXAMPLE 7

3-{Difluoro[(4-fluorophenyl)sulfonyl]methyl}-1-[2-(2,4-difluorophenyl)ethyl]azetidine hydrochloride Prepared in an analogous manner to Example 6, Step 3 using tert-butyl 3-{difluoro[(4-fluorophenyl)sulfonyl]methyl}azetidine-1-carboxylate (Example 6, Step 2).

$^1$H NMR (400 MHz, CD$_3$OD) δ 2.97 (2H, t, J=7.8 Hz), 3.52–3.55 (2H, m), 4.06–4.16 (1H, m), 4.50 (4H, br s), 6.96–7.03 (2H, m), 7.37–7.42 (1H, m), 7.53 (2H, t, J=8.7 Hz), 8.10–8.12 (2H, m). m/z (ES$^+$) 406 (M+H)$^+$.

EXAMPLE 8

6-Fluoro-3-[(3-{[(4-fluorophenyl)sulfonyl]methyl}azetidin-1-yl)methyl]-1,2-benzisothiazole hydrochloride Step 1: 3-Bromomethyl-6-fluoro-1,2-benzisothiazole A mixture of 6-fluoro-3-methyl-1,2-benzisothiazole [prepared by the method of D. M. Fink and J. T. Strupczewski, Tetrahedron Lett., 1993, 34, 6525] (761 mg, 4.55 mmol), N-bromosuccinimide (0.89 g, 5.0 mmol) and benzoyl peroxide (102 mg 70% (w/w)), 0.29 mmol) in CCl$_4$ (25 mL) was heated at reflux under nitrogen for 6 h. The mixture was allowed to cool and filtered under suction. The filtrate was concentrated and the residue purified by flash silica chromatography, eluting with 1:2 then 1:1 DCM/isohexane to give the title compound as a white solid (569 mg, 51%). $^1$H NMR (500 MHz, CDCl$_3$) δ 4.82 (3H, s), 7.25 (1H, dt, J=8.8 and 2.2 Hz), 7.60 (1H, dd, J=8.1 and 2.2 Hz), 8.07–8.10 (1H, m). (471 MHz, CDCl$_3$)δ$_F$ –111.9.

Step 2: 6-Fluoro-3-[(3-{[(4-fluorophenyl)sulfonyl]methyl}azetidin-1-yl)methyl]-1,2-benzisothiazole hydrochloride 3-Bromomethyl-6-fluoro-1,2-benzisothiazole (73 mg, 0.3 mmol) was added to a mixture of 3-{[(4-fluorophenyl)sulfonyl]methyl}azetidine hydrochloride (57 mg, 0.21 mmol) and potassium carbonate (91 mg, 0.66 mmol) in DMF (2 mL) and the resulting mixture stirred at room temperature for 18 h. The mixture was diluted with 0.5M sodium hydroxide solution (20 mL) and extracted with EtOAc (2×10 mL). The organic extracts were washed with saturated brine (10 mL), combined, dried (MgSO$_4$) and concentrated. The residue was purified by preparative thin layer chromatography, eluting with 2.5% MeOH/DCM, to afford an oil which crystallised on standing (35 mg, 41%). The solid was dissolved in EtOAc, the resulting solution heated and treated with 1M HCl in diethyl ether (0.11 mL). The mixture was allowed to cool to give a crystalline solid which was collected under suction to afford the title compound (21 mg). $^1$H NMR (400 MHz, CD$_3$OD) δ 3.33–3.41 (1H, m), 3.72 (2H, d, J=7.6 Hz), 4.23–4.28 (2H, m), 4.44–4.49 (2H, m), 4.96 (2H, s), 7.35–7.46 (3H, m), 7.87–7.90 (1H, m), 7.99–8.04 (2H, m), 8.10–8.13 (1H, m). (471 MHz, CD$_3$OD)δ$_F$ –105.2, –112.7. m/z (ES$^+$) 395 (M+H)$^+$.

EXAMPLE 9

6-Fluoro-3-[(3-{[(4-fluorophenyl)sulfonyl]methyl}azetidin-1-yl)methyl]-1,2-benzisoxazole hydrochloride Prepared in an analogous manner to Example 8, using 6-fluoro-3-methyl-1,2-benzisoxazole [prepared by the method of G. T. Theodoridis, L. L. Maravetz and S. D. Crawford, WO 97/12886].

$^1$H NMR (500 MHz, CD$_3$OD) δ 3.32–3.40 (1H, m), 3.73 (2H, d, J=7.6 Hz), 4.29–4.33 (2H, m), 4.45–4.49 (2H, m), 4.98 (2H, s), 7.29 (1H, dt, J=9.0 and 2.0 Hz), 7.41–7.45 (2H, m), 7.54 (1H, dd, J=8.6 and 2.0 Hz), 7.90 (1H, dd, J=8.8 and 4.9 Hz), 8.00–8.03 (2H, m). (471 MHz, CD$_3$OD) δ$_F$ –105.1, –109.3. m/z (ES$^+$) 379 (M+H)$^+$.

EXAMPLE 10

1-(4-Fluoro-2-methylphenyl)-2-(3-{[(4-fluorophenyl)sulfonyl]methyl}azetidin-1-yl)ethanone Step 1: 1-(4-Fluoro-2-methylphenyl)ethanone To a solution of 2-bromo-5-fluorotoluene (5 g, 26.5 mmol) in DMF (65 ml) and water (15 ml) was added butyl vinyl ether (6.6 g, 65.9 mmol), palladium acetate (0.18 g, 0.8 mmol), 1,3-bis(diphenylphosphino)propane (0.72 g, 1.75 mmol) and potassium carbonate (4.4 g, 31.8 mmol). The reaction was heated at 80° C. for 48 h under nitrogen. The cooled reaction mixture was diluted with EtOAc (~250 ml) and concentrated HCl added and shaken. Further EtOAc and water were added to obtain an easier separation of the 2 layers. The organic layer was washed with brine, dried (MgSO$_4$), and concentrated. The residue was purified on a plug of silica eluting with 3% EtOAc/isohexane to give the title compound as an oil (1.95 g, 49%). ¹H NMR (400 MHz, d₆-DMSO) δ 2.45 (3H, s), 2.54 (3H, s), 7.13–7.17 (2H, m), 7.89–7.93 (1H, m).

Step 2: 2-Bromo-1-(4-fluoro-2-methylphenyl)ethanone

A solution of the foregoing acetophenone (1.95 g, 12.8 mmol) in THF (35 ml) was treated with phenyltrimethylammonium tribromide (4.82 g, 12.8 mmol) portionwise. Upon complete addition the suspension was stirred for a further 20 min then water (150 ml) was added. The mixture was extracted twice with EtOAc. The combined organics were dried (MgSO₄) and concentrated. The residue was purified on a silica plug column using 2% EtOAc/isohexane to give the title compound as a yellow oil (1.96 g, 66%). ¹H NMR (400 MHz, d₆-DMSO) δ 2.43 (3H, s), 4.85 (2H, s), 7.16–7.24 (2H, m), 7.95–7.99 (1H, dd, J=6.0 & 8.6 Hz).

Step 3: 1-(4-Fluoro-2-methylphenyl)-2-(3-{[(4-fluorophenyl)sulfonyl]methyl}azetidin-1-yl)ethanone A mixture of 3-{[(4-fluorophenyl)sulfonyl]methyl}azetidine hydrochloride (75 mg, 0.28 mmol) in MeCN (5 mL) was treated with Et₃N (97 μL, 0.7 mmol) and 2-bromo-1-(4-fluoro-2-methylphenyl)ethanone (72 mg, 0.31 mmol) and stirred for 30 min at room temperature. The reaction was evaporated and the residue dissolved in DCM and purified using 10 g silica bond-elute cartridge on the personal flash master. The column was eluted with 0.5% MeOH/DCM then 1% MeOH/DCM to give the title compound as a cream solid (60 mg, 56%). ¹H NMR (500 MHz, CDCl₃) δ 2.49 (3H, s), 2.93–2.98 (1H, m), 3.08 (2H, t, J=7.4 Hz), 3.41 (2H, d, J=7.4 Hz), 3.62 (2H, t, J=7.4 Hz), 3.77 (2H, s), 6.89–6.95 (2H, m), 7.23–7.27 (2H, t, J=8.8 Hz), 7.61 (1H, dd, J=5.8 & 8.5 Hz), 7.90–7.92 (2H, dd, J=5.2 & 8.8 Hz). m/z (ES⁺) 380 (M+H)⁺.

EXAMPLE 11

1-(4-Fluorophenyl)-2-(3-{[(2-fluorophenyl)sulfonyl]methyl}azetidin-1-yl)ethanone hydrochloride Step 1: 1-(Diphenylmethyl)-3-{[(2-fluorophenyl)sulfonyl]methyl}azetidine

[1-(Diphenylmethyl)azetidin-3-yl]methyl methanesulfonate [Example 1, step 1] (3.15 g, 9.50 mmol), sodium 2-fluorobenzenesulfinate (2.65 g, 14.3 mmol) and sodium iodide (2.18 g, 14.5 mmol) were reacted in dimethylformamide (50 mL) by the procedure of Example I Step 3a to afford the title compound (1.37 g, 36%); ¹H NMR (500 MHz, CDCl₃) δ 2.80–2.88 (3H, m), 3.33 (2H, t, J=7.0 Hz), 3.57 (2H, d, J=6.9 Hz), 4.28 (1H, s), 7.16 (2H, t, J=7.3 Hz), 7.20–7.26 (5H, m), 7.29–7.35 (5H, m), 7.61–7.65 (1H, m), 7.86–7.90 (1H, m); ¹⁹F NMR (471 MHz, CDCl₃) δ –108.9; m/z (ES⁺) 396 ([M+H]⁺, 100%).

Step 2: 3-{[(2-Fluorophenyl)sulfonyl]methyl}azetidine hydrochloride 1-(Diphenylmethyl)-3-{[(2-fluorophenyl)sulfonyl]methyl}azetidine (1.33 g, 3.37 mmol) was dissolved in ethanol (80 mL). The solution was diluted with 2M hydrochloric acid (1.8 mL) and water (20 mL). 20% Palladium hydroxide on carbon (0.63 g) was added and the mixture shaken on a Parr apparatus under 50 psi of hydrogen for 3.5 h. The catalyst was removed by filtration and the filtrate concentrated to a small volume. The solid present was redissolved by adding ethanol and the solution filtered. The filtrate was concentrated to a small volume once again to give a crystalline solid which was collected under suction, washed with cold ethanol and dried in vacuo to afford the title compound as colourless crystals (0.81 g, 91%); ¹H NMR (500 MHz, CD₃OD) δ 3.34–3.42 (1H, m), 3.80 (2H, d, J=7.6 Hz), 4.07 (2H, t, J=10 Hz), 4.14 (2H, t, J=10 Hz), 7.41–7.49 (2H, m), 7.80–7.84 (1H, m), 7.90–7.92 (1H, m); ¹⁹F NMR (471 MHz, CD₃OD) δ –110.6; m/z (ES⁺) 230 ([M+H]⁺, 100%).

Step 3: 1-(4-Fluorophenyl)-2-(3-{[(2-fluorophenyl)sulfonyl]methyl}azetidin-1-yl)ethanone hydrochloride Triethylamine (135 μL, 0.97 mmol) was added to a suspension of 3-{[(2-fluorophenyl)sulfonyl]methyl}azetidine hydrochloride (101 mg, 0.38 mmol) in acetonitrile (5 mL) and the mixture stirred for 3 minutes. 2-Bromo-4'-fluorophenylacetophenone (88 mg, 0.41 mmol) was added and the resulting mixture stirred at room temperature for 30 minutes. The reaction mixture was concentrated in vacuo at ambient temperature, treated with water (20 mL) and saturated sodium hydrogen carbonate (1 mL) and extracted with ethyl acetate (2×25 mL). The extracts were washed with brine (20 mL), combined, dried (MgSO₄) and evaporated. The residue was purified by preparative thin layer chromatography, eluting with 2:1 ethyl acetate/dichloromethane, to afford an oil (100 mg). This oil was dissolved in ethyl acetate and treated with 1M hydrogen chloride in diethyl ether (330 μL) to give a gum. Trituration with warming afforded a solid which was collected under suction, washed with ethyl acetate and dried in vacuo to give the title compound as a white solid (92 mg, 60%); ¹H NMR (500 MHz, DMSO-d₆) δ 3.11–3.17 (1H, m), 3.98 (2H, m), 4.12 (2H, m), 4.24 (2H, t, J=9.6 Hz), 5.11 (2H, s), 7.45 (2H, t, J=8.7 Hz), 7.53 (1H, t, J=7.6 Hz), 7.59 (1H, t, J=9.4 Hz), 7.85–7.91 (2H, m), 8.01 (2H, dd, J=5.5, 8.4 Hz), 11.04 (1H, s); ¹⁹ F NMR (471 MHz, DMSO-d₆) δ –103.4, –109.3; m/z (ES⁺) 366 ([M+H]⁺, 100%).

EXAMPLES 12–18

Following the procedure of Example 10 Step 3, using the appropriate 2-bromoacetophenone, the following were obtained:

EXAMPLE 12

1-(4-chlorophenyl)-2-(3-{[(4-fluorophenyl)sulfonyl]methyl}azetidin-1-yl)ethanone ¹H NMR (500 MHz, CDCl₃) δ 2.94–2.98 (1H, m), 3.08 (2H, t, J=7.5 Hz), 3.41 (2H, d, J=7.5 Hz), 3.61 (2H, t, J=7.5 Hz), 3.86 (2H, s), 7.25 (2H, m), 7.42 (2H, d, J=8.6 Hz), 7.83 (2H, d, J=8.6 Hz), 7.91 (2H, dd, J=5.0 & 8.8 Hz). m/z (ES⁺) 382 & 384 (M+H)⁺.

EXAMPLE 13

1-(2-chloro-4-fluorophenyl)-2-(3-{[(4-fluorophenyl)sulfonyl]methyl}azetidin-1-yl)ethanone ¹H NMR (500 MHz, CDCl₃) δ 2.92–2.97 (1H, m), 3.08 (2H, t, J=7.5 Hz), 3.40 (2H, d, J=7.5 Hz), 3.59 (2H, t, J=7.5 Hz), 3.83 (2H, s), 7.03–7.05 (1H, m), 7.15 (1H, dd, J=2.4 & 8.4), 7.25 (2H, m), 7.56 (1H, dd, J=6.0 & 8.7 Hz), 7.91 (2H, dd, J=5.2 & 8.5 Hz). m/z (ES⁺) 400 & 402 (M+H)⁺.

EXAMPLE 14

1-(3,4-difluorophenyl)-2-(3-{[(4-fluorophenyl)sulfonyl]methyl}azetidin-1-yl)ethanone ¹H NMR (500 MHz, CDCl₃) δ 2.94–2.98 (1H, m), 3.08 (2H, t, J=7.5 Hz), 3.40 (2H, d, J=7.5 Hz), 3.60 (2H, t, J=7.5

Hz), 3.84 (2H, s), 7.02–7.27 (3H, m), 7.66–7.69 (1H, m), 7.73–7.77 (1H, m), 7.91 (2H, dd, J=5.0 & 8.8 Hz). m/z (ES⁺) 384 (M+H)⁺.

EXAMPLE 15

1-(4-bromophenyl)-2-(3-{[(4-fluorophenyl)sulfonyl]methyl}azetidin-1-yl)ethanone

¹H NMR (500 MHz, CDCl₃) δ 2.94–2.97 (1H, m), 3.08 (2H, t, J=7.5 Hz), 3.41 (2H, d, J=7.5 Hz), 3.61 (2H, t, J=7.5 Hz), 3.86 (2H, s), 7.23–7.27 (2H, m), 7.59 (2H, d, J=8.7 Hz), 7.75 (2H, d, J=8.7 Hz), 7.91 (2H, dd, J=5.0 & 8.9 Hz). m/z (ES⁺) 426 & 428 (M+H)⁺.

EXAMPLE 16

2-(3-{[(4-fluorophenyl)sulfonyl]methyl}azetidin-1-yl)-1-phenylethanone

¹H NMR (360 MHz, CDCl₃) δ 2.94–3.00 (1H, m), 3.09 (2H, t, J=7.5 Hz), 3.42 (2H, d, J=7.5 Hz), 3.62 (2H, t, J=7.5 Hz), 3.92 (2H, s), 7.22–7.28 (2H, m), 7.46 (2H, t, J=8.0 Hz), 7.54–7.58 (1H, m), 7.86–7.94 (4H, m). m/z (ES⁺) 348 (M+H)⁺.

EXAMPLE 17

1-(2-chlorophenyl)-2-(3-{[(4-fluorophenyl)sulfonyl]methyl}azetidin-1-yl)ethanone ¹H NMR (500 MHz, CDCl₃) δ 2.90–2.98 (1H, m), 3.08 (2H, t, J=7.5 Hz), 3.41 (2H, d, J=7.5 Hz), 3.60 (2H, t, J=7.5 Hz), 3.83 (2H, s), 7.23–7.28 (2H, m), 7.29–7.32 (1H, m), 7.38–7.40 (2H, m), 7.44 (1H, d, J=8.2 Hz), 7.91 (2H, dd, J=5.0 & 8.8 Hz). m/z (ES⁺) 382 & 384 (M+H)⁺.

EXAMPLE 18

1-(2-bromo-4-fluorophenyl)-2-(3-{[(4-fluorophenyl)sulfonyl]methyl}azetidin-1-yl)ethanone ¹H NMR (500 MHz, CDCl₃) δ 2.91–2.98 (1H, m), 3.10 (2H, t, J=7.5 Hz), 3.40 (2H, d, J=7.5 Hz), 3.61 (2H, t, J=7.5 Hz), 3.80 (2H, s), 7.06–7.10 (1H, m), 7.24–7.28 (2H, m), 7.35 (1H, dd, J=2.4 & 8.2 Hz), 7.42 (1H, dd, J=5.8 & 8.6 Hz), 7.91 (2H, dd, 5.0 & 8.8 Hz). m/z (ES⁺) 444 & 446 (M+H)⁺.

EXAMPLE 19

4-[({1-[2-(4-Fluorophenyl)-2-oxoethyl]azetidin-3-yl}methyl)sulfonyl]benzonitrile Step 1: tert-Butyl 3-{[(methylsulfonyl)oxy]methyl}azetidine-1-carboxylate

[1-(Diphenylmethyl)azetidin-3-yl]methyl methanesulfonate [Example 1, Step 1] (3.0 g, 9.09 mmol), 5 M HCl (1.8 mL, 9.09 mmol), H₂O (5 mL), EtOH (100 mL) and 20% Pd(OH)₂ (500 mg) were combined and shaken for 3 h under hydrogen (40 psi) on a Parr machine. The catalyst was removed by filtration and filtrate concentrated in vacuo. The residue was azeotroped with EtOH followed by Et₂O to give a colourless gum which was dissolved in DCM (50 mL) and treated with di-tert-butyl dicarbonate (2.0 g, 9.09 mmol) and Et₃N (2.5 mL, 18.2 mmol) at 0° C. The resulting mixture was stirred for 2 h at room temperature. The mixture was washed with saturated brine and the organic layer separated, dried (MgSO₄) and concentrated in vacuo. The residue was purified using column chromatography, on silica gel, eluting with 1:1 EtOAc:isohexane to give the title product as a colourless gum (2.02 g, 84%). ¹H NMR (500 MHz, CDCl₃) δ 1.44 (9H, s), 2.89–2.97 (1H, m), 3.05 (3H, s), 3.72 (2H, dd, J=5.1, 8.9 Hz), 4.05 (2H, t, J=8.6 Hz), 4.35 (2H, d, J=6.8 Hz).

Step 2: tert-Butyl 3-{[(4-cyanophenyl)thio]methyl}azetidine-1-carboxylate

A solution of the foregoing mesylate (1 g, 3.9 mmol) in MeCN (30 ml) was degassed with N₂ and then K₂CO₃ (1.08 g, 7.8 mmol) and 4-cyanothiophenol (585 mg, 4.36 mmol) were added and the reaction heated to 80° C. for 3h. The reaction was evaporated and the residue partitioned between DCM and water, retaining the DCM layer. The aqueous layer was re-extracted with DCM and the combined organics were washed with brine then dried (MgSO₄) and evaporated. The residue was purified using plug silica chromatography eluting with 20% EtOAc/isohexane then 40% EtOAc/isohexane. The title compound was isolated as a white solid (1 g, 83%). ¹H NMR (400 MHz, CDCl₃) δ 1.44 (9H, s), 2.70–2.79 (1H, m), 3.21 (2H, d, J=7.8 Hz), 3.66 (2H, dd, J=5.2 & 8.9 Hz), 4.05 (2H, t, J=8.4 Hz) 7.32 (2H, d, J=8.5 Hz), 7.54 (2H, d, J=8.5 Hz).

Step 3: tert-Butyl 3-{[(4-cyanophenyl)sulfonyl]methyl}azetidine-1-carboxylate

A mixture of the foregoing sulfide (1 g, 3.3 mmol), DCM (50 ml) and NaHCO₃ (1.38 g, 16.6 mmol) was cooled in an ice/water bath and treated with meta-chloroperoxybenzoic acid (77%) (1.84 g, 8.3 mmol) portionwise. After the addition was complete the cooling bath was removed and the reaction stirred for a further 2 h. Water was added and the mixture was transferred to a separation funnel. The DCM layer was separated and the aqueous re-extracted with DCM. Combined organics washed with K₂CO₃ solution, then brine and dried (MgSO₄) and evaporated to give the title compound as a white solid (1 g, 91%). %). ¹H NMR (500 MHz, CDCl₃) δ 1.42 (9H, s), 2.95–3.05 (1H, m), 3.42 (2H, d, J=7.5 Hz), 3.66–3.72 (2H, m), 4.08 (2H, t, J=8.4 Hz), 7.89 (2H, d, J=8.2 Hz), 8.02 (2H, d, J=8.2 Hz).

Step 4: 4-[(Azetidin-3-ylmethyl)sulfonyl]benzonitrile hydrochloride

The foregoing tert-butyl 3-{[(4-cyanophenyl)sulfonyl]methyl}azetidine-1-carboxylate (200 mg, 0.59 mmol) was treated with 4N HCl in 1,4-dioxane and stirred for 10 minutes. The reaction was evaporated without heat to give the title compound crude as a white solid (100 mg). ¹H NMR (500 MHz, CDCl₃) δ 2.99–3.05 (1H, m), 3.78 (2H, t, J=7.8 Hz), 3.86–3.94 (4H, m), 8.08 (2H, d, J=8.6 Hz), 8.20 (2H, d, J=8.6 Hz), 8.95 (2H, br s).

Step 5: 4-[({1-[2-(4-Fluorophenyl)-2-oxoethyl]azetidin-3-yl}methyl)sulfonyl]benzonitrile Following the procedure of Example 2, 4-[(azetidin-3-ylmethyl)sulfonyl]benzonitrile hydrochloride (75 mg, 0.27 mmol) was reacted with 2-bromo-1-(4-fluorophenyl)ethanone. Crude product was purified on a 10 g bond elute silica cartridge using the personal flash master eluting with 0.5% MeOH/DCM to 2% MeOH/DCM to give the freebase as a pale yellow gum (30 mg, 29%). The freebase was dissolved in 3:1 ether/MeOH (5 ml) and 1.0M hydrogen chloride in ether (89μl) was added. The side of the flask was etched and the salt precipitated and was isolated by filtration and dried under vacuum to give the title compound as a white solid (20 mg). ¹H NMR (500 MHz, CDCl₃) δ 3.05–3.13 (1H, m), 3.90–3.96 (2H, m), 4.03–4.12 (2H, m), 4.23–4.30 (2H, m), 5.06 (2H, s), 7.44 (2H, t, J=8.8 Hz), 8.01 (2H, dd, J=5.4 & 8.8 Hz), 8.09 (2H, d, J=8.6 Hz), 8.21 (2H, d, J=8.6 Hz), 10.62 (1H, s). m/z (ES$^+$) 373 (M+H)$^+$.

EXAMPLE 20

2-{1-[2-(2,4-Difluorophenyl)ethyl]azetidin-3-yl}-1-phenylethanone

Step 1: Methyl{1-[2-(2,4-difluorophenyl)ethyl]azetidin-3-yl}acetate

A mixture of [1-(tert-butoxycarbonyl)azetidin-3-yl]acetic acid (2 g, 9.24 mmol), potassium carbonate (1.54 g, 11.1 mmol) and methyl iodide (2.89 mL, 46.5 mmol) in N,N-dimethylformamide (30 mL) was stirred at room temperature under nitrogen overnight. The reaction mixture was diluted with water and extracted with dichloromethane (x2). The combined organic layers were washed with saturated sodium hydrogencarbonate solution, dried over MgSO$_4$ and concentrated in vacuo. The residue was dissolved in dichloromethane (5 mL) and trifluoroacetic acid (5 mL) added. The reaction was stirred at room temperature for 30 minutes. The solvent was removed in vacuo. The residue was dissolved in N,N-dimethylformamide (30 mL). 2,4-Difluorophenethyl bromide (2.26 g, 10.2 mmol) and potassium carbonate (5.14 g, 37.2 mmol) were added and the reaction heated at 60° C. overnight. The cooled reaction mixture was diluted with water and extracted with dichloromethane (x3). The combined organic layers were washed with brine, dried over MgSO$_4$ and concentrated in vacuo. The residue was purified by flash column chromatography on silica, eluting with 5% methanol/dichloromethane, to give methyl{1-[2-(2,4-difluorophenyl)ethyl]azetidin-3-yl}acetate (1.3 g, 52%). $^1$H NMR (360 MHz, CDCl$_3$) δ 7.15–7.09 (1H, m), 6.79–6.71 (2H, m), 3.64 (3H, s), 3.48–3.44 (2H, m), 2.87–2.75 (3H, m), 2.60 (4H, s), 2.57 (2H, d, J=7.1 Hz); m/z (ES$^+$) 270 (M+H)$^+$.

Step 2: 2-{1-[2-(2,4-Difluorophenyl)ethyl]azetidin-3-yl}-N,N-dimethoxyacetamide

A slurry of methyl{1-[2-(2,4-difluorophenyl)ethyl]azetidin-3-yl}acetate (Step 1, 0.5 g, 1.86 mmol) and N,O-dimethylhydroxylamine hydrochloride (272 mg, 2.79 mmol) in tetrahydrofuran (4 mL) was cooled to −20° C. under nitrogen. Isopropylmagnesium chloride (2M in tetrahydrofuran, 2.79 mL, 5.57 mmol) was added dropwise, maintaining the internal temperature between −20 and −5° C. The reaction was stirred at −20° C. for 30 minutes then at room temperature for 2.5 hours. Saturated ammonium chloride solution was added and the mixture stirred vigorously for 5 minutes then extracted with ethyl acetate (x3). The combined organic layers were dried over MgSO$_4$ and concentrated in vacuo. The residue was purified by flash column chromatography on silica, eluting with 7% methanol/dichloromethane, to give 2-{1-[2-(2,4-difluorophenyl)ethyl]azetidin-3-yl}-N,N-dimethoxyacetamide (297 mg, 54%). $^1$H NMR (400 MHz, CDCl$_3$) δ 7.16–7.10 (1H, m), 6.79–6.71 (2H, m), 3.67 (3H, s), 3.51–3.47 (2H, m), 3.14 (3H, s), 2.89–2.79 (3H, m), 2.71 (2H, d, J=6.8 Hz), 2.62 (4H, s); m/z (ES$^+$) 299 (M+H)$^+$.

Step 3: 2-{1-[2-(2,4-Difluorophenyl)ethyl]azetidin-3-yl}1-1-phenylethanone

A solution of methyl 2-{1-[2-(2,4-difluorophenyl)ethyl] azetidin-3-yl}-N,N-dimethoxyacetamide (Step 2, 200 mg, 0.67 mmol) in tetrahydrofuran (4 mL) was cooled to −78° C. under nitrogen. Phenylmagnesium bromide (1M in tetrahydrofuran, 1.34 mL, 1.34 mmol) was added dropwise, maintaining the internal temperature below −50° C. The reaction was stirred at −78° C. for 15 minutes then allowed to warm to room temperature overnight. Saturated ammonium chloride solution was added and the mixture stirred vigorously for 5 minutes then extracted with ethyl acetate (x3). The combined organic layers were washed with brine, dried over MgSO$_4$ and concentrated in vacuo. The residue was purified by flash column chromatography on silica, eluting with 5% methanol/dichloromethane, to give the title compound as a pale yellow oil. This was dissolved in ethyl acetate and treated with ethereal HCl then recrystallised from ethyl acetate to give the hydrochloride salt (121 mg, 51%). $^1$H NMR (400 MHz, CD$_3$OD) δ 7.99–7.97 (2H, m), 7.64–7.60 (1H, m), 7.52–7.48 (2H, m), 7.40–7.34 (1H, m), 7.02–6.94 (2H, m), 4.34 (2H, t, J=9.7 Hz), 3.98 (2H, t, J=8.8 Hz), 3.51–3.45 (4H, m), 3.39–3.28 (1H, m), 2.93 (2H, t, J=7.6 Hz); m/z (ES$^+$) 316 (M+H)$^+$.

EXAMPLE 21

2-{1-[2-(2,4-Difluorophenyl)ethyl]azetidin-3-yl}-1-phenylethanol

To a solution of 2-{1-[2-(2,4-difluorophenyl)ethyl]azetidin-3-yl}-1-phenylethanone (Example 20, 41 mg, 0.117 mmol) in methanol (1 mL) under nitrogen was added sodium borohydride (8.8 mg, 0.23 mmol). The reaction was stirred at room temperature overnight. More sodium borohydride (5 mg, 0.13 mmol) was added and the reaction stirred for 30 minutes. More sodium borohydride (8.8 mg, 0.23 mmol) was added and the reaction stirred for 15 minutes. More sodium borohydride (5 mg, 0.13 mmol) was added and the reaction stirred overnight. The solvent was removed in vacuo and the residue purified by flash column chromatography on silica, eluting with 10% methanol/dichloromethane, to give the title compound. $^1$H NMR (360 MHz, CDCl$_3$) δ 7.35–7.29 (5H, m), 7.22–7.16 (1H, m), 6.81–6.73 (2H, m), 4.71 (1H, dd, J=5.3, 7.6 Hz), 3.63 (1H, s), 3.53 (1H, s), 3.11 (1H, s), 2.98 (1H, s), 2.77 (5H, s), 2.07–1.92 (2H, m); m/z (ES$^+$) 318 (M+H)$^+$.

EXAMPLE 22

1-[2-(2,4-Difluorophenyl)-2-fluoroethyl]-3-{[(4-fluorophenyl)sulfonyl]methyl}azetidine Step 1:1-(2,4-Difluorophenyl)-2-(3-{[(4-fluorophenyl)sulfonyl]methyl}azetidin-1-yl)ethanol Triethylamine (210 μL, 1.52 mmol) was added to a stirred suspension of 3-{[(4-fluorophenyl)sulfonyl]methyl}azetidine hydrochloride (Example 1 Step 4, 270 mg, 1.02 mmol) in acetonitrile (3 mL) under nitrogen. 2-(2,4-Difluorophenyl)oxirane (WO 99/23083; 1:1 mixture of enantiomers, 238 mg, 1.52 mmol) was added followed by lithium perchlorate (110 mg, 1.03 mmol). The resulting solution was stirred overnight at room temperature. The reaction mixture was poured into water and extracted with dichloromethane (x3). The combined organic layers were washed with water (x3) and brine, dried over MgSO$_4$ and evaporated in vacuo. The residue was triturated with diethyl ether/isohexane then with 5% methanol/ethyl acetate to give 1-(2,4-difluorophenyl)-2-(3-{[(4-fluorophenyl)sulfonyl] methyl}azetidin-1-yl)ethanol (134 mg, 34%). $^1$H NMR (500 MHz, CD$_3$OD) δ 7.96–7.92 (2H, m), 7.50–7.46 (1H, m), 7.39–7.33 (2H, m), 6.93–6.91 (1H, m), 6.88–6.84 (1H, m), 3.48 (2H, d, J=7.3 Hz), 3.44–3.38 (2H, m), 2.96–2.88 (2H, m), 2.83–2.75 (1H, m), 2.67–2.61 (2H, m); m/z (ES$^+$) 386 (M+H)$^+$.

Step 2: 1-[2-(2,4-Difluorophenyl)-2-fluoroethyl]-3-{[(4-fluorophenyl)sulfonyl]methyl}azetidine A stirred suspension of the alcohol from Step 1 (130 mg, 0.33 mmol) in dichloromethane (4 mL) under nitrogen was cooled to −10° C. (Diethylamino)sulfur trifluoride (54 μL, 0.41 mmol) was added dropwise and after 30 minutes the cooling bath was removed. After a further 15 minutes, the reaction was quenched with saturated aqueous sodium hydrogencarbonate solution and extracted with dichloromethane. The combined organic layers were washed with water and brine, dried over MgSO$_4$ and evaporated in vacuo. The residue was purified by preparative TLC (50% ethyl acetate/isohexane) to give the title compound (64 mg, 50%). $^1$H NMR (500 MHz, CDCl$_3$) δ 7.91–7.89 (2H, m), 7.40–7.34 (1H, m), 7.27–7.23 (2H, m), 6.90 (1H, t, J=8.2 Hz), 6.79 (1H, t, J=9.5 Hz), 5.70–5.58 (1H, m), 3.49 (2H, q, J=7.4 Hz), 3.38–3.36 (2H, m), 2.95 (2H, q, J=6.7 Hz), 2.90–2.70 (3H, m); m/z (ES$^+$) 388 (M+H)$^+$.

EXAMPLE 23

1-[(6-Fluoro-1-benzothien-3-yl)methyl]-3-{[(4-fluorophenyl)sulfonyl]methyl}azetidine Sodium cyanoborohydride (13 mg, 0.20 mmol) was added to a stirred solution of 3-{[(4-fluorophenyl)sulfonyl]methyl}azetidine hydrochloride (Example 1 Step 4, 49 mg, 0.18 mmol) and 6-fluoro-1-benzothiophene-3-carbaldehyde (36 mg, 0.20 mmol) in methanol (3 mL) and acetic acid (50 μL). The reaction was stirred at room temperature for 4 hours. The solvent was removed in vacuo and the residue partitioned between sodium carbonate and ethyl acetate. The aqueous layer was extracted with further ethyl acetate and the combined organic layers washed with water and brine, dried over MgSO$_4$ and evaporated. The residue was purified by preparative TLC (40% ethyl acetate/isohexane) to give the title compound which was treated with ethereal HCl to give the hydrochloride salt (46 mg, 59%). $^1$H NMR (400 MHz, CD$_3$OD) δ 8.00–7.96 (3H, m), 7.88 (1H, s), 7.74 (1H, dd, J=2.4, 8.8 Hz), 7.43–7.37 (2H, m), 7.31–7.27 (1H, m), 4.68 (2H, s), 4.24 (2H, s), 4.16 (2H, t, J=9.7 Hz), 3.67 (2H, d, J=7.6 Hz), 3.30–3.22 (1H, m); m/z (ES$^+$) 394 (M+H)$^+$.

EXAMPLE 24

1-[(3-{[(4-Fluorophenyl)sulfonyl]methyl}azetidin-1-yl)methyl]isoquinoline dihydrochloride Prepared by the procedure of Example 8, Step 2, using 1-(bromomethyl)isoquinoline hydrobromide.

$^1$H NMR (500 MHz, CD$_3$OD) δ 3.38–3.50 (1H, m), 3.76 (H, d, J=7.6 Hz), 4.31 (2H, t, J=10 Hz), 4.52 (2H, t, J=10 Hz), 5.25 (2H, s), 7.40–7.46 (2H, m), 7.75–7.79 (1H, m), 7.82–7.87 (2H, m), 8.00–8.05 (3H, m), 8.10 (1H, d, J=8.3 Hz), 8.48 (1H, d, J=5.8 Hz). m/z (ES$^+$) 371 (M+H)$^+$.

EXAMPLE 25

1-[(6-Chloro-1-benzothien-3-yl)methyl]-3-{[(4-fluorophenyl)sulfonyl]methyl}azetidine Prepared according to the method of Example 23 using 3-{[(4-fluorophenyl)sulfonyl]methyl}azetidine hydrochloride (Example 1 Step 4) and 6-chloro-1-benzothiophene-3-carbaldehyde. $^1$H NMR (500 MHz, CDCl$_3$) δ 7.92–7.88 (2H, m), 7.81 (1H, d, J=1.8 Hz), 7.72 (1H, d, J=8.5 Hz), 7.32 (1H, dd, J=1.9, 8.6 Hz), 7.26–7.22 (2H, m), 7.19 (1H, s), 3.73 (2H, s), 3.44 (2H, t, J=7.5 Hz), 3.37 (2H, d, J=7.3 Hz), 2.92 (2H, t, J=7.1 Hz), 2.87–2.80 (1H, m). m/z (ES$^+$) 394 (M+H)$^+$.

EXAMPLE 26

1-[(2S)-2-(2,4-Difluorophenyl)-2-fluoroethyl]-3-{[(4-fluorophenyl)sulfonyl]methyl}azetidine Prepared according to the method of Example 22 using the (R)-enantiomer of the oxirane. $^1$H NMR (500 MHz, CD$_3$OD) δ 8.02–7.98 (2H, m), 7.59–7.53 (1H, m), 7.45–7.39 (2H, m), 7.12–7.08 (2H, m), 6.06–5.94 (1H, m), 4.42–4.36 (2H, m), 4.21 (2H, s), 3.95 (1H, q, J=12.2 Hz), 3.73–3.63 (3H, m), 3.36–3.30 (2H, m); m/z (ES$^+$) 388 (M+H)$^+$.

EXAMPLE 27

1-[(2R)-2-(2,4-Difluorophenyl)-2-fluoroethyl]-3-{[(4-fluorophenyl)sulfonyl]methyl}azetidine Prepared according to the method of Example 22 using the (S)-enantiomer of the oxirane. $^1$H NMR (500 MHz, CD$_3$OD) δ 8.02–7.98 (2H, m), 7.59–7.53 (1H, m), 7.45–7.39 (2H, m), 7.12–7.08 (2H, m), 6.06–5.94 (1H, m), 4.42–4.36 (2H, m), 4.21 (2H, s), 3.95 (1H, q, J=12.2 Hz), 3.73–3.63 (3H, m), 3.36–3.30 (2H, m); m/z (ES$^+$) 388 (M+H)$^+$.

EXAMPLE 28

3-{[(4-Fluorophenyl)sulfonyl]methyl}1-(4,5,6,7-tetrahydro-1-benzothien-3-ylmethyl)azetidine Step 1: 4,5,6,7-Tetrahydro-1-benzothien-3-ylmethanol A solution of 4,5,6,7-tetrahydro-1-benzothiophene-3-carboxylic acid (400 mg, 2.2 mmol) in diethyl ether (10 mL) was added under nitrogen to lithium aluminium hydride (1M solution in tetrahydrofuran, 3 mL, 3 mmol) in diethyl ether (10 mL) dropwise over 5 minutes. The reaction was stirred at room temperature for 1.5 hours then quenched with saturated ammonium chloride solution. The products were extracted into diethyl ether (x3). The combined organic layers were washed with water and brine, dried over MgSO$_4$ and evaporated in vacuo to give 4,5,6,7-tetrahydro-1-benzothien-3-ylmethanol (320 mg, 86%). $^1$H NMR (500 MHz, CDCl$_3$) δ 6.99 (1H, s), 4.56 (2H, s), 2.76 (2H, t, J=5.5 Hz), 2.58 (2H, t, J=5.6 Hz), 1.86–1.79 (4H, m), 1.43 (1H, s).

Step 2: 4,5,6,7-Tetrahydro-1-benzothiophene-3-carbaldehyde

A solution of 4,5,6,7-tetrahydro-1-benzothien-3-ylmethanol (Step 1, 320 mg, 1.9 mmol) in dichloromethane (10 mL) was added to a stirred solution of 1,1,1-tris(acetyloxy)-1,1-dihydro-1,2-benziodoxol-3-(1H)-one (0.92 g, 2.1 mmol) in dichloromethane (10 mL) under nitrogen and stirred at room temperature for 20 minutes. Diethyl ether (50 mL) and 1N sodium hydroxide solution (25 mL) were added and the mixture stirred vigorously for 15 minutes. The organic layer was washed with sodium hydroxide, water and brine, dried over MgSO$_4$ and evaporated in vacuo to give 4,5,6,7-tetrahydro-1-benzothiophene-3-carbaldehyde (280 mg, 88%). $^1$H NMR (360 MHz, CDCl$_3$) δ 9.88 (1H, s), 7.85 (1H, s), 2.92–2.88 (2H, m), 2.76 (2H, t, J=6.0 Hz), 1.88–1.76 (4H, m).

Step 3: 3-{[(4-Fluorophenyl)sulfonyl]methyl}1-(4,5,6,7-tetrahydro-1-benzothien-3-ylmethyl)azetidine The title compound was prepared from the product of Step 2 using the method of Example 23. $^1$H NMR (500 MHz, CD$_3$OD) δ 8.00–7.96 (2H, m), 7.43–7.39 (2H, m), 7.33 (1H, s), 4.26 (2H, s), 4.20 (2H, t, J=10.0 Hz), 4.07 (2H, t, J=9.7 Hz), 3.63 (2H, d, J=7.5 Hz), 3.26–3.20 (1H, m), 2.76 (2H, s), 2.56 (2H, s), 1.84–1.82 (4H, m); m/z (ES$^+$) 380 (M+H)$^+$.

EXAMPLE 29

3-{[(4-Fluorophenyl)sulfonyl]methyl}1-(thieno[2,3-b]thien-3-ylmethyl)azetidine

Step 1: 3-Methylthieno[2,3-b]thiophene

A 1M solution of 1-(2-thienylthio)acetone (2.6 g, 15.1 mmol) in chlorobenzene (15 mL) was heated to 110° C. under nitrogen and hot polyphosphoric acid (3 mL) was added. The reaction was heated to reflux overnight. The chlorobenzene layer was decanted off and further chlorobenzene (15 mL x2) was added to the polyphosphoric acid residue and stirred at reflux for 30 minutes. The combined chlorobenzene extracts were concentrated in vacuo and purified by flash column chromatography on silica, eluting with 40% dichloromethane/isohexane, to give 3-methylthieno[2,3-b]thiophene (0.97 g, 42%). $^1$H NMR (500 MHz, CDCl$_3$) δ 7.34 (1H, dd, J=1.0, 5.2 Hz), 7.16 (1H, d, J=5.2 Hz), 6.94 (1H, t, J=1.1 Hz), 2.40 (3H, d, J=1.1 Hz).

Step 2: 2-Bromo-3-methylthieno[2,3-b]thiophene

3-Methylthieno[2,3-b]thiophene (Step 1, 450 mg, 2.92 mmol) was dissolved in carbon tetrachloride (7 mL) under nitrogen. N-Bromosuccinimide (0.52 g, 2.92 mmol) and benzoyl peroxide (75% in water; 0.10 g, 0.29 mmol) were added and the reaction heated to reflux for 6 hours. The solvent was removed in vacuo and the residue taken up in dichloromethane then filtered onto a column of silica and eluted with isohexane to give 2-bromo-3-methylthieno[2,3-b]thiophene (0.25 g, 37%). $^1$H NMR (500 MHz, CDCl$_3$) δ 7.38 (1H, d, J=5.2 Hz), 7.13 (1H, d, J=5.2 Hz), 2.34 (3H, s).

Step 3: 2,5-Dibromo-3-(bromomethyl)thieno [2,3-b]thiophene

Step 2 was repeated on 2-bromo-3-methylthieno[2,3-b]thiophene (Step 2) to give 2,5-dibromo-3-(bromomethyl)thieno[2,3-b]thiophene. $^1$H NMR (500 MHz, CDCl$_3$) δ 7.31 (1H, s), 4.55 (2H, s).

Step 4: 1-[(2,5-Dibromothieno[2,3-b]thien-3-yl)methyl]-3-{[(4-fluorophenyl)sulfonyl]methyl}azetidine Prepared from 3-{[(4-fluorophenyl)sulfonyl]methyl}azetidine hydrochloride (Example 1 Step 4) and 2,5-dibromo-3-(bromomethyl)thieno[2,3-b]thiophene (Step 3) according to the method of Example 1 Step 5. $^1$H NMR (500 MHz, CDCl$_3$) δ 7.90–7.88 (2H, m), 7.33 (1H, s), 7.26–7.23 (2H, m), 3.60 (2H, s), 3.40 (2H, t, J=7.4 Hz), 3.35 (2H, d, J=7.3 Hz), 2.90 (2H, t, J=7.0 Hz), 2.84–2.77 (1H, m); m/z (ES$^+$) 540 (M+H)$^+$.

Step 5: 3-{[(4-Fluorophenyl)sulfonyl]methyl}1-(thieno[2,3-b]thien-3-ylmethyl)azetidine A mixture of 1-[(2,5-dibromothieno[2,3-b]thien-3-yl)methyl]-3-{[(4-fluorophenyl)sulfonyl]methyl}azetidine (Step 4, 39 mg, 0.07 mmol) and 10% palladium on carbon (50 mg) in methanol (7 mL) was stirred under a balloon of hydrogen for 3.5 hours. The catalyst was removed by filtration through Celite®, washing with methanol after the addition of triethylamine (30 μL) to quench any HBr formed. The filtrate was concentrated in vacuo. The residue was purified by preparative TLC (50% ethyl acetate/isohexane) to give the title compound (2.5 mg). $^1$H NMR (500 MHz, CDCl$_3$) δ 7.91–7.89 (2H, m), 7.34 (1H, dd, J=1.0, 5.2 Hz), 7.23 (3H, t, J=7.3 Hz), 7.10 (1H, s), 3.70 (2H, s), 3.47 (2H, t, J=7.3 Hz), 3.38 (2H, d, J=7.3 Hz), 2.96 (2H, br s), 2.88–2.82 (1H, m).

EXAMPLE 30

1-[(2-Fluoro-1-benzothien-3-ylmethyl]-3-{[(4-fluorophenyl)sulfonyl]methyl}azetidine Step 1: 3-(Bromomethyl)-2-fluoro-1-benzothiophene A stirred solution of 3-methylbenzothiophene (0.51 g, 3.37 mmol) in acetonitrile (5 μL) under nitrogen was treated with SELECTFLUOR™ (1.25 g, 3.35 mmol) and heated to 70° C. overnight. The solvent was removed in vacuo. The residue was taken up in ethyl acetate and washed with sodium hydrogen carbonate solution, water and brine, dried over MgSO$_4$ and evaporated in vacuo. Purification by flash column chromatography on silica, eluting with isohexane, gave 2-fluoro-3-methyl-1-benzothiophene (72% pure, 190 mg, 0.82 mmol) which was treated according to the method of Example 29 Step 2 to give 3-(bromomethyl)-2-fluoro-1-benzothiophene (95 mg, 12%). $^1$H NMR (500 MHz, CDCl$_3$) δ 7.75 (1H, d, J=8.0 Hz), 7.68 (1H, d, J=8.0 Hz), 7.46 (1H, t, J=7.6 Hz), 7.39–7.35 (1H, m), 4.65 (2H, s).

Step 2: 1-[(2-Fluoro-1-benzothien-3-ylmethyl]-3-{[(4-fluorophenyl)sulfonyl]methyl}azetidine Prepared from the product of Step 1 using the method of Example 1 Step 5. $^1$H NMR (500 MHz, CDCl$_3$) δ 7.88 (2H, dd, J=6.1, 8.4 Hz), 7.71 (H, d, J=7.8 Hz), 7.64 (1H, d, J=7.8 Hz), 7.36 (1H, t, J=7.7 Hz), 7.30 (1H, t, J=7.6 Hz), 7.22 (2H, d, J=8.3 Hz), 3.67 (2H, s), 3.42 (2H, t, J=7.1 Hz), 3.34 (2H, d, J=7.3 Hz), 2.95–2.88 (2H, m), 2.82–2.76 (1H, m); m/z (ES$^+$) 394 (M+H)$^+$.

EXAMPLE 31

1-(4-Fluoro-2-hydroxyphenyl)-2-(3-{[(4-fluorophenyl)sulfonyl]methyl}azetidin-1-yl)ethanone Step 1: 2-Bromo-1-(4-fluoro-2-methoxyphenyl)ethanone 4-Fluoro-2-methoxyacetophenone (1 g, 5.95 mmol) was brominated as described in Example 10 Step 2. Dry flash chromatography of the crude product, eluting with 3–5% ethyl acetate/isohexane, gave 2-bromo-1-(4-fluoro-2-methoxyphenyl)ethanone as a pale yellow oil (1.37 g, 93%). $^1$H NMR (400 MHz, d$_6$-DMSO) δ 7.77 (1H, dd, J=7.0, 8.8 Hz), 7.13 (1H, dd, J=2.4, 11.4 Hz), 6.92–6.88 (1H, m), 4.75 (2H, s), 3.92 (3H, s).

Step 2: 1-(4-Fluoro-2-methoxyphenyl)-2-(3-{[(4-fluorophenyl)sulfonyl]methyl}azetidin-1-yl)ethanone Prepared from 2-bromo-1-(4-fluoro-2-methoxyphenyl) ethanone (Step 1) according to the method of Example 2. $^1$H NMR (500 MHz, d$_6$-DMSO) δ 10.38 (1H, s), 7.95 (2H, s), 7.90 (1H, t, J=7.9 Hz), 7.54 (2H, t, J=8.7 Hz), 7.19 (1H, d, J=9.3 Hz), 6.95 (1H, t, J=7.3 Hz), 4.80–4.77 (2H, m), 4.22–4.15 (2H, m), 4.05–3.98 (2H, m), 3.96 (3H, s), 3.83 (2H, dd, J=6.5, 48.0 Hz), 3.07–3.02 (1H, m); m/z (ES$^+$) 396 (M+H)$^+$.

Step 3: 1-(4-Fluoro-2-hydroxyphenyl)-2-(3-{[(4-fluorophenyl)sulfonyl]methyl}azetidin-1-yl)ethanone To a solution of 1-(4-fluoro-2-methoxyphenyl)-2-(3-{[(4-fluorophenyl)sulfonyl]methyl}azetidin-1-yl)ethanone (Step 2, 49.4 mg, 0.125 mmol) in dichloromethane (1 mL) at 0° C. was added boron tribromide (1M in dichloromethane, 0.5 mL, 0.5 mmol). The reaction was stirred at 0° C. for 30 minutes. Diethyl ether (5 mL) was added and the resulting slurry partitioned between saturated sodium carbonate solution and ethyl acetate. Water was added to dissolve some of the resulting precipitate and the biphasic mixture was decanted from the remaining solid. The aqueous layer was extracted with ethyl acetate and the combined organic layers were washed with water and brine, dried over $MgSO_4$ and concentrated in vacuo. The residue was purified by flash column chromatography on silica, eluting with ethyl acetate, to give the title compound which was treated with ethereal HCl to give the hydrochloride salt (10.5 mg, 20%). $^1$H NMR (500 MHz, $d_6$-DMSO) δ 11.83 (1H, s), 10.34 (1H, s), 7.95 (2H, dd, J=5.3, 8.2 Hz), 7.83 (1H, dd, J=7.3, 8.5 Hz), 7.54 (2H, t, J=8.7 Hz), 6.91 (1H, dd, J=2.0, 10.7 Hz), 6.81–6.79 (1H, m), 4.83 (2H, s), 4.19 (2H, br s), 4.05–3.97 (2H, m), 3.87–3.78 (2H, m), 3.08–3.02 (1H, m); m/z (ES$^+$) 382 (M+H)$^+$.

EXAMPLE 32

2-(3-{[(4-Fluorophenyl)sulfonyl]methyl}azetidin-1-yl)-1-(3-thienyl)ethanone

Prepared according to the method of Example 2 using 3-{[(4-fluorophenyl)sulfonyl]methyl}azetidine hydrochloride (Example 1 Step 4) and 2-bromo-1-(3-thienyl)ethanone. $^1$H NMR (500 MHz, $d_6$-DMSO) δ 10.51 (1H, s), 8.52 (1H, s), 7.96 (2H, dd, J=5.1, 8.7 Hz), 7.72 (1H, dd, J=2.8, 5.0 Hz), 7.55 (2H, t, J=8.8 Hz), 7.49 (1H, d, J=4.3 Hz), 4.91 (2H, s), 4.19 (2H, s), 4.00 (2H, s), 3.82 (2H, d, J=6.7 Hz), 3.10–3.03 (1H, m); m/z (ES$^+$) 354 (M+H)$^+$.

EXAMPLE 33

2-(3-{[(3-Bromophenyl)sulfonyl]methyl}azetidin-1-yl)-1-(4-fluorophenyl)ethanone

Prepared by the procedure of Example 19 using 3-bromothiophenol I place of 4-cyanothiophenol. $^1$H NMR (500 MHz, $d_6$-DMSO) δ 10.63 (1H, s), 8.04–7.98 (4H, m), 7.90 (1H, d, J=7.8 Hz), 7.66 (1H, t, J=7.9 Hz), 7.44 (2H, t, J=8.8 Hz), 5.07 (2H, s), 4.25 (2H, s), 4.06 (2H, s), 3.89 (2H, s), 3.09 (1H, s), 2.05 (1H, s). m/z (ES$^+$) 427 (M+H)$^+$.

EXAMPLE 34

6-Fluoro-3-[(3-{[(1-methyl-1H-imidazol-2-yl)sulfonyl]methyl}azetidin-1-yl)methyl]-1,2-benzisothiazole Step 1: tert-Butyl 3-{[(1-methyl-1H-imidazol-2-yl)thio]methyl}azetidine-1-carboxylate Prepared as in Example 19 Steps 1 and 2, using 2-mercapto-1-methylimidazole in place of 4-cyanothiophenol in Step 2.

The crude product was purified using column chromatography on silica gel, eluting with 25% EtOAc in DCM to afford the title product as a colourless oil. $^1$H NMR (400 MHz, CDCl$_3$) δ 1.43 (9H, s), 2.76–2.86 (1H, m), 3.27 (2H, d, J=7.7 Hz), 3.59–3.61 (5H, m), 4.00 (2H, t, J=8.5 Hz), 6.92 (1H, d, J=1.2 Hz), 7.05 (1H, d, J=1.2 Hz).

Step 2: tert-Butyl 3-{[(1-methyl-1H-imidazol-2-yl)sulfonyl]methyl}azetidine-1-carboxylate A mixture of the foregoing sulfide (0.37 g, 1.3 mmol), Oxone® (2.39 g, 3.9 mmol) and wet alumina (1.19 g with 0.5 mL water) in DCM (10 mL) was stirred overnight. Solids were removed by filtration and the filtrate washed with saturated brine, dried (MgSO$_4$) and concentrated in vacuo to give the title product as a colourless oil (0.30 g, 73%). $^1$H NMR (400 MHz, CDCl$_3$) δ 1.43 (9H, s), 3.10–3.20 (1H, m), 3.76 (4H, m), 3.98 (3H, s), 4.11 (2H, t, J=8.7 Hz), 7.01 (1H, s), 7.14 (1H, d, J=1.0 Hz).

Step 3: 2-[(Azetidin-3-ylmethyl)sulfonyl]-1-methyl-1H-imidazole

The foregoing sulfone (50 mg, 0.16 mmol) was dissolved in DCM (0.5 mL) and TFA (0.5 mL) was added. The resulting mixture was stirred for 30 min then concentrated in vacuo yielding the bis(trifluoroacetate) salt. The colourless oil was converted to the free base using a SCX cartridge, eluting with methanol followed by 2 M ammonia in methanol, affording the title compound as a colourless oil (30 mg, 87%). $^1$H NMR (400 MHz, CD$_3$OD) δ 3.16–3.26 (1H, m), 3.51 (2H, t, J=8.3 Hz), 3.68–3.72 (4H, m), 4.00 (3H, s), 7.17 (1H, d, J=0.9 Hz), 7.38 (1H, d, J=0.9 Hz). m/z (ES$^+$) 216 (M+H)$^+$.

Step 4: 6-Fluoro-3-[(3-{[(1-methyl-1H-imidazol-2-yl)sulfonyl]methyl}azetidin-1-yl)methyl]-1,2-benzisothiazole Prepared from the product of Step 3 using the procedure of Example 8 Step 2. $^1$H NMR (400 MHz, CD$_3$OD) δ 8.15 (1H, dd, J=4.6, 8.7 Hz), 7.77 (1H, dd, J=2.3, 8.8 Hz), 7.37 (1H, d, J=1.0 Hz), 7.30–7.26 (1H, m), 7.16 (1H, d, J=1.0 Hz), 4.06 (2H, s), 3.99 (3H, s), 3.71 (2H, d, J=7.4 Hz), 3.56 (2H, t, J=7.9 Hz), 3.15–3.11 (2H, m), 2.98–2.90 (1H, m). m/z (ES$^+$) 381 (M+H)$^+$.

EXAMPLE 35

2-[({1-[2-(2,4-Difluorophenyl)ethyl]azetidin-3-yl}methyl)sulfonyl]-1-methyl-1H-imidazole Step 1: (2,4-Difluorophenyl)acetaldehyde To a solution of 2,4-difluorophenylacetonitrile (3.0 g, 19 mmol) in anhydrous DCM (40 mL), cooled to −78° C., was added DIBAL (40 mL, 1 M in DCM) dropwise. The resulting mixture was allowed to warm to room temperature overnight. Excess reagent was quenched with ethyl formate (1.6 mL). After 1.5 h the mixture was poured into saturated NH$_4$Cl (300 mL) then treated with 2 M H$_2$SO$_4$ (100 mL). The mixture was extracted with Et$_2$O. The extracts were washed with water and saturated brine and dried (MgSO$_4$). Toluene was added and solvent removed at <30° C. on high vacuum to a final volume of ~30 mL. The solution of the crude aldehyde, approx. 100 mg/mL, was used without further purification.

Step 2: 2-[({1-[2-(2,4-Difluorophenyl)ethyl]azetidin-3-yl}methyl)sulfonyl]-1-methyl-1H-imidazole A solution of crude (2,4-difluorophenyl)acetaldehyde in toluene (0.75 mL, 100 mg/mL) was concentrated in vacuo, then 2-[(azetidin-3-ylmethyl)sulfonyl]-1-methyl-1H-imidazole (Example 34 Step 3) (52 mg, 0.23 mmol), NaCNBH$_3$ (32.0 mg, 0.54 mmol) and MeOH (2 mL) were added. The resulting mixture was stirred overnight. The reaction mixture was partitioned between 0.5 N NaOH (20 mL) and EtOAc (20 mL). The aqueous phase was washed with EtOAc (20 mL) and the organic layers were combined, washed with saturated brine (20 mL), dried (MgSO$_4$) and concentrated in vacuo. The residue was purified using preparative HPLC with UV detection eluting with 30% MeCN/ 0.1% TFA in H$_2$O. Further purification using a SCX cartridge eluting with methanol followed by 2 M ammonia in methanol, afforded the title compound (3 mg, 4%). $^1$H NMR (400 MHz, CD$_3$OD) δ 2.77 (2H, t, J=7.4 Hz), 3.16–3.02 (3H, m), 3.46 (2H, m), 3.75 (2H, d, J=7.4 Hz), 3.83 (2H, m), 3.99 (3H, s), 6.98–6.90 (2H, m), 7.17 (1H, s), 7.34–7.28 (1H, m), 7.39 (1H, s). m/z (ES$^+$) 356 (M+H)$^+$.

EXAMPLE 36

3-({3-[(1,3-Thiazol-2-ylsulfonyl)methyl]azetidin-1-yl}methyl)-1,2-benzisothiazole Step 1: tert-Butyl 3-[(1,3-thiazol-2-ylsulfonyl)methyl]azetidine-1-carboxylate Prepared as in Example 34 Steps 1 and 2, using 2-mercaptothiazole in place of 2-mercapto-1-methylimidazole.

Product isolated as a colourless oil. $^1$H NMR (360 MHz, CDCl$_3$) δ 1.42 (9H, s), 3.05–3.15 (1H, m), 3.72 (4H, d, J=7.4 Hz), 4.10 (2H, t, J=8.7 Hz), 7.78 (1H, d, J=3.0 Hz), 8.08 (1H, d, J=3.0 Hz).

Step 2: 3-({3-[(1,3-Thiazol-2-ylsulfonyl)methyl]azetidin-1-yl}methyl)-1,2-benzisothiazole tert-Butyl 3-[(1,3-thiazol-2-ylsulfonyl)methyl]azetidine-1-carboxylate (51 mg, 0.16 mmol) was dissolved in DCM (0.5 mL) and TFA (0.5 mL) was added. The resulting mixture was stirred for 30 min. then concentrated in vacuo. The residual oil was taken up in MeOH (2 mL), then NaCNBH$_3$ (16.2 mg, 0.26 mmol) and 1,2-benzisothiazole-3-carbaldehyde (28.6 mg, 0.18 mmol) [prepared by the method of T. Hasegawa, Y. Akiyama, T. Imai, E. Sato, Y. Yamamoto, J. Tanaka, H. Nagaso, K. Fuji, K. Murase, M. Shiiyama, WO 98/08816] were added. The mixture was stirred overnight then partitioned between 0.5 N NaOH (20 mL) and EtOAc (20 mL). The aqueous phase was washed with EtOAc (20 mL) and the organic layers were combined, washed with saturated brine (20 mL), dried (MgSO$_4$) and concentrated in vacuo. The residue was purified using column chromatography, on silica gel, eluting with 50–60% EtOAc in DCM to give the title compound as a colourless oil (19 mg, 29%). $^1$H NMR (400 MHz, CDCl$_3$) δ 2.96–3.06 (1H, m), 3.12 (2H, m), 3.57 (2H, t, J=7.6 Hz), 3.72 (2H, d, J=7.3 Hz), 4.04 (2H, s), 7.41–7.45 (1H, m), 7.50–7.54 (1H, m), 7.74 (1H, d, J=3.1 Hz), 7.91 (1H, d, J=8.2 Hz), 8.05 (1H, d, J=3.0 Hz), 8.10 (1H, d, J=8.1 Hz). m/z (ES$^+$) 366 (M+H)$^+$.

EXAMPLE 37

2-[({1-[2-(2,4-Difluorophenyl)ethyl]azetidin-3-yl}methyl)sulfonyl]-1,3-thiazole

Prepared by a combination of Example 36 Step 1 and Example 35 Step 2. $^1$H NMR (400 MHz, CDCl$_3$) δ 2.59 (4H, s), 2.87–2.99 (3H, m), 3.42–3.48 (2H, m), 3.68 (2H, d, J=7.0 Hz), 6.72–6.80 (2H, m), 7.08–7.16 (1H, m), 7.75 (1H, d, J=3.1 Hz), 8.06 (1H, d, J=3.1 Hz). m/z (ES$^+$) 359 (M+H)$^+$.

EXAMPLE 38

3-[(3-{[(2,4-Difluorophenyl)sulfinyl]methyl}azetidin-1-yl)methyl]-1,2-benzisothiazole Step 1: tert-Butyl 3-{[(2,4-difluorophenyl)thio]methyl}azetidine-1-carboxylate Prepared by the procedure of Example 19 Steps 1 and 2, using 2,4-difluorothiophenol in Step 2 to afford the title product as a yellow oil. $^1$H NMR (360 MHz, CDCl$_3$) δ 1.43 (9H, s), 2.55–2.65 (1H, m), 3.03 (2H, d, J=7.8 Hz), 3.61 (2H, dd, J=5.4, 8.8 Hz), 3.99 (2H, t, J=8.5 Hz), 6.82–6.88 (2H, m), 7.38–7.44 (1H, m).

Step 2: tert-Butyl 3-{[(2,4-difluorophenyl)sulfinyl]methyl}azetidine-1-carboxylate The foregoing sulfide (0.43 g, 1.4 mmol) in DCM (2 mL) was added to a vigorously stirred slurry of oxone® (0.85 g, 1.4 mmol) and wet alumina (1.37 g, prepared as described in Synlett, 1992, 235) in DCM (8 mL). The resulting mixture was stirred at reflux overnight. The cooled reaction mixture was filtered, the residue washed with DCM and the filtrate plus washings concentrated in vacuo. The residue was purified using column chromatography on silica gel, eluting with 10–20% EtOAc in DCM to yield the title product as a colourless glass which solidified on standing (0.34 g, 74%). $^1$H NMR (500 MHz, CDCl$_3$) δ 1.42 (9H, s), 3.02–3.08 (1H, m), 3.13 (1H, dd, J=7.2, 13.3 Hz), 3.28 (1H, dd, J=7.4, 13.3 Hz), 3.52 (1H, s), 3.79 (1H, dd, J=5.6, 8.6 Hz), 3.92 (1H, s), 4.16 (1H, t, J=7.2 Hz), 6.89–6.93 (1H, m), 7.12–7.16 (1H, m), 7.76–7.82 (1H, m).

Step 3: 3-[(3-{[(2,4-Difluorophenyl)sulfinyl]methyl}azetidin-1-yl)methyl]-1,2-benzisothiazole Prepared from the product of Step 2 using the procedure of Example 36 Step 2 to afford the title compound as a colourless oil. $^1$H NMR (500 MHz, CDCl$_3$) δ 2.96–3.02 (2H, m), 3.12 (1H, dd, J=6.3, 13.1 Hz), 3.19 (1H, t, J=6.7 Hz), 3.29 (1H, dd, J=6.6, 13.2 Hz), 3.42 (1H, t, J=6.6 Hz), 3.64 (1H, t, J=7.1 Hz), 4.03 (2H, s), 6.86–6.90 (1H, m), 7.09–7.13 (1H, m), 7.42 (1H, t, J=7.5 Hz), 7.50–7.52 (1H, m), 7.77–7.81 (1H, m), 7.91 (1H, d, J=8.1 Hz), 8.10 (1H, d, J=8.1 Hz). m/z (ES$^+$) 379 (M+H)$^+$.

EXAMPLE 39

1-[2-(2,4-Difluorophenyl)ethyl]-3-{[(2,4-difluorophenyl)sulfinyl]methyl}azetidine Prepared via deprotection of the product of Example 38 Step 2 (as described in Example 34 Step 3), followed by reductive amination as described in Example 35 Step 2 to yield the title compound as a colourless glass. $^1$H NMR (400 MHz, CDCl$_3$) δ 2.59 (4H, s), 2.75 (1H, t, J=6.5 Hz), 2.91–2.99 (2H, m), 3.08 (1H, dd, J=6.5, 13.5 Hz), 3.23–3.29 (2H, m), 3.49–3.53 (1H, m), 6.72–6.80 (2H, m), 6.86–6.90 (1H, m), 7.08–7.14 (2H, m), 7.76–7.82 (1H, m). m/z (ES$^+$) 372 (M+H)$^+$.

EXAMPLE 40

4-[({1-[2-(2,4-Difluorophenyl)ethyl]azetidin-3-yl}methyl)sulfonyl]pyridine

Step 1: tert-Butyl 3-[(pyridin-4-ylthio)methyl]azetidine-1-carboxylate

Prepared as in Example 19 Steps 1 and 2, using 4-mercaptopyridine to afford the title product as a colourless gum. $^1$H NMR (400 MHz, CDCl$_3$) δ 1.44 (9H, s), 2.75–2.85 (1H, m), 3.22 (2H, d, J=7.8 Hz), 3.68 (2H, dd, J=5.2, 9.0 Hz), 4.07 (2H, t, J=8.5 Hz), 7.11 (2H, dd, J=1.6, 4.7 Hz), 8.41 (2H, dd, J=1.6, 4.6 Hz).

Step 2: tert-Butyl 3-[(pyridin-4-ylsulfonyl)methyl]azetidine-1-carboxylate

The foregoing sulfide (237 mg, 0.84 mmol) was mixed with 4-methylmorpholine-N-oxide (474 mg) in THF (10 mL), then $OsO_4$ (2 mL, 4 wt. % in water) was added. The resulting mixture was stirred for 3 days. Excess reagent was quenched with 1M $Na_2SO_3$ solution then the reaction mixture was filtered using celite. The filtrate was partitioned between EtOAc (200 mL) and saturated brine (200 mL), the aqueous phase washed with EtOAc (100 mL) then the organic layers were combined, washed with brine (100 mL), dried ($MgSO_4$), filtered through celite and concentrated in vacuo. The residue was purified using column chromatography on silica gel, eluting with EtOAc to give the title product as a colourless oil (52 mg, 20%). $^1$H NMR (400 MHz, $CDCl_3$) δ 1.42 (9H, s), 2.95–3.05 (1H, m), 3.41 (2H, d, J=7.5 Hz), 3.70 (2H, m), 4.10 (2H, t, J=8.7 Hz), 7.76 (2H, dd, J=1.6, 4.4 Hz), 8.95 (2H, dd, J=1.5, 4.5 Hz).

Step 3: 4-[({1-[2-(2,4-Difluorophenyl)ethyl]azetidin-3-yl}methyl)sulfonyl]pyridine Prepared from the product of Step 2 by the procedure of Example 39 to give the title compound as a colourless oil (25 mg, 42%). $^1$H NMR (400 MHz, $CDCl_3$) δ 2.58 (4H, s), 2.80–2.88 (3H, m), 3.39–3.43 (4H, m), 6.72–6.80 (2H, m), 7.07–7.13 (1H, m), 7.75 (2H, dd, J=1.7, 4.4 Hz), 8.92 (2H, dd, J=1.6, 4.4 Hz). m/z (ES)$^+$ 353 (M+H)$^+$.

What is claimed is:

1. A compound of the formula I:

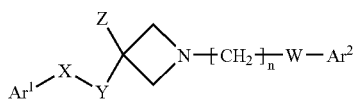

I wherein n is 0, 1, 2 or 3;
W is $CH_2$, CO, CHF or CH(OH);
X is $SO_2$, SO, CO or CH(OH);
Y is $CH_2$, CHF or $CF_2$;
Z is H, F or OH;
$Ar^1$ is phenyl or heteroaryl, wherein heteroaryl is selected from thiazole, imidazole and triazole, and wherein said phenyl or heteroaryl is unsubstituted or substituted with up to 3 substituents selected from halogen, CN, $NO_2$, $R^1$, $OR^2$, $COR^2$, $CO_2R^2$, $OCOR^1$, $SR^2$, $S(O)_tR^1$ where t is 1 or 2, $N(R^2)_2$, $CON(R^2)_2$, $NR^2COR^1$ and $SO_2N(R^2)_2$;
$Ar^2$ is a mono- or bicyclic ring system selected from phenyl, naphthyl, pyrrole, oxazole, isoxazole, thiazole, isothiazole, and imidazole, and their benzo-fused and tetrahydrobenzo-fused derivatives, wherein said ring system is unsubstituted or substituted with up to 3 substituents selected from halogen, CN, $NO_2$, $R^1$ and $OR^2$;
$R^1$ is $C_{1-6}$alkyl or phenyl, which is unsubstituted or substituted with up to 5 fluorine substituents; and
$R^2$ is $R^1$ or H; or two $R^2$ groups attached to the same nitrogen atom may form a pyrrolidine, imidazole or triazole ring,
or a pharmaceutically acceptable salt or hydrate thereof.

2. The compound of claim 1 wherein W is $CH_2$, CHF or CO.

3. The compound of claim 1 wherein X is $SO_2$ or SO.

4. The compound of claim 1 of formula II:

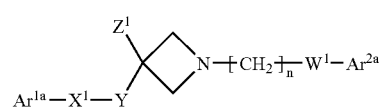

II wherein:
$W^1$ is $CH_2$ or CO;
$Z^1$ is H or F;
$X^1$ is SO or $SO_2$;
$Ar^{1a}$ is phenyl which is unsubstituted or substituted with up to 2 substituents selected from F, Cl, Br, CN, methyl, $CF_3$, methoxy, $CF_3O$ and $CONH_2$;
$Ar^{2a}$ is phenyl, pyrrole, oxazole, isoxazole, thiazole, isothiazole, imidazole, benzisothiazolyl or benisoxazolyl, which is unsubstituted or substituted with up to 2 substituents selected from F, Cl, Br, OH and $C_{1-4}$alkyl;
or a pharmaceutically acceptable salt or hydrate thereof.

5. The compound of claim 4 wherein n is 1; $X^1$ is $SO_2$; $Z^1$ is H; $Ar^{1a}$ is phenyl which is unsubstituted or substituted with up to 2 substituents selected from F, Cl, Br and CN; and $Ar^{2a}$ is phenyl which is unsubstituted or substituted with up to 2 substituents selected from F, Cl, Br, OH and methyl.

6. The compound of claim 5 wherein n is 1; $X^1$ is $SO_2$; $Z^1$ is $Ar^{1a}$ is 2-fluorophenyl, 4-fluorophenyl or 2,4-difluorophenyl; and $Ar^{2a}$ is 4-fluorophenyl, 2,4-difluorophenyl or 4-fluoro-2-methylphenyl.

7. The compound of claim 4 of formula III:

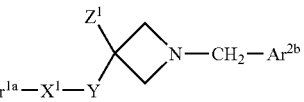

III wherein:
$Ar^{2b}$ represents benzisothiazolyl or benisoxazolyl, which is unsubstituted or substituted with up to 2 substituents selected from F, Cl, Br, OH and $C_{1-4}$alkyl;
or a pharmaceutically acceptable salt or hydrate thereof.

8. The compound of claim 7 wherein $X^1$ is $SO_2$; $Z^1$ is H; Y is $CH_2$; $Ar^{1a}$ is phenyl which bears up to 2 substituents selected from F, Cl, Br and CN; and $A^{2a}$ is benzisothiazolyl or benisoxazolyl optionally bearing up to 2 substituents slected from F, Cl, Br, OH and methyl.

9. The compound of claim 1 which is selected from:
1-[2-(2,4-difluorophenyl)ethyl]-3-{[(4-fluorophenyl)sulfonyl]methyl}azetidine;
1-(4-fluorophenyl)-4-(3-{[(4-fluorophenyl)sulfonyl]methyl}azetidin-1-yl)butan-1-one;
1-(4-fluorophenyl)-2-(3-{[(4-fluorophenyl)sulfonyl]methyl}azetidin-1-yl)ethanone;
2-(3-{[(2,4-difluorophenyl)sulfonyl]methyl}azetidin-1-yl)-1-(4-fluorophenyl)ethanone;
2-(3-fluoro-3-{[(4-fluorophenyl)sulfonyl]methyl}azetidin-1-yl)-1-(4-fluorophenyl)ethanone;
1-[2-(2,4-difluorophenyl)ethyl]-3-{fluoro[(4-fluorophenyl)sulfonyl]methyl}azetidine;
3-{difluoro[(4-fluorophenyl)sulfonyl]methyl}-1-[2-(2,4-difluorophenyl)ethyl]azetidine;

6-fluoro-3-[(3-{[(4-fluorophenyl)sulfonyl]
methyl}azetidin-1-yl)methyl]-1,2-benzisothiazole;
6-fluoro-3-[(3-{[(4-fluorophenyl)sulfonyl]
methyl}azetidin-1-yl)methyl]-1,2-benzisoxazole;
1-(4-fluoro-2-methylphenyl)-2-(3-{[(4-fluorophenyl)sulfonyl]methyl}azetidin-1-yl)ethanone;
1-(4-fluorophenyl)-2-(3-{[(2-fluorophenyl)sulfonyl]
methyl}azetidin-1-yl)ethanone;
or a pharmaceutically acceptable salt or hydrate thereof.

10. The compound of claim 9 which is in the form of the hydrochloride salt, the methansulfonate salt, or the benzenesulfonate salt.

11. A compound which is:
1-(4-fluorophenyl)-4-(3-{[(4-fluorophenyl)sulfonyl]
methyl}azetidin-1-yl)butan-1-one;
or a pharmaceutically acceptable salt or hydrate thereof.

12. A compound which is:
1-(4-fluorophenyl)-2-(3-{[(4-fluorophenyl)sulfonyl]
methyl}azetidin-1-yl)ethanone;
or a pharmaceutically acceptable salt or hydrate thereof.

13. A compound which is:
6-fluoro-3-[(3-{[(4-fluorophenyl)sulfonyl]
methyl}azetidin-1-yl)methyl]-1,2-benzisothiazole;
or a pharmaceutically acceptable salt or hydrate thereof.

14. A pharmaceutical composition comprising a compound of claim 1 and a pharmaceutically acceptable carrier.

15. A pharmaceutical composition comprising a compound of claim 9 and a pharmaceutically acceptable carrier.

16. A pharmaceutical composition comprising a compound of claim 11 and a pharmaceutically acceptable carrier.

17. A pharmaceutical composition comprising a compound of claim 12 and a pharmaceutically acceptable carrier.

18. A pharmaceutical composition comprising a compound of claim 13 and a pharmaceutically acceptable carrier.

19. A method for the treatment of a sleep disorder in a human subject which comprises administering to that subject an effective amount of the compound of claim 1, or a pharmaceutically acceptable salt or hydrate thereof.

20. A method for the treatment of a sleep disorder in a human subject which comprises administering to that subject an effective amount of the compound of claim 9, or a pharmaceutically acceptable salt or hydrate thereof.

21. A method for the treatment of a sleep disorder in a human subject which comprises administering to that subject an effective amount of the compound of claim 11, or a pharmaceutically acceptable salt or hydrate thereof.

22. A method for the treatment of a sleep disorder in a human subject which comprises administering to that subject an effective amount of the compound of claim 12, or a pharmaceutically acceptable salt or hydrate thereof.

23. A method for the treatment of a sleep disorder in a human subject which comprises administering to that subject an effective amount of the compound of claim 13, or a pharmaceutically acceptable salt or hydrate thereof.

24. A process for the preparation of a compound of claim 1 comprising reaction of a compound of formula:

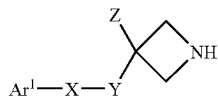

with a compound of formula:

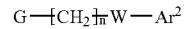

wherein G is a leaving group and n, W, X, Y, Z, $Ar^1$ and $Ar^2$ are as defined in claim 1.

* * * * *